(12) United States Patent
Mehal et al.

(10) Patent No.: US 9,415,046 B2
(45) Date of Patent: Aug. 16, 2016

(54) COMPOSITIONS AND METHODS FOR INHIBITING INFLAMMATION FROM AND REJECTION OF BIOMATERIALS AND OTHER METHODS

(75) Inventors: Wajahat Z. Mehal, Guilford, CT (US); Themis Kyriakides, Branford, CT (US)

(73) Assignee: YALE UNIVERSITY, New Haven, CT (US)

(*) Notice: Subject to any disclaimer, the term of this patent is extended or adjusted under 35 U.S.C. 154(b) by 379 days.

(21) Appl. No.: 13/496,009

(22) PCT Filed: Sep. 28, 2010

(86) PCT No.: PCT/US2010/050544
§ 371 (c)(1),
(2), (4) Date: May 24, 2012

(87) PCT Pub. No.: WO2011/041311
PCT Pub. Date: Apr. 7, 2011

(65) Prior Publication Data
US 2012/0225931 A1    Sep. 6, 2012

Related U.S. Application Data

(60) Provisional application No. 61/281,823, filed on Nov. 23, 2009, provisional application No. 61/277,798, filed on Sep. 29, 2009.

(51) Int. Cl.
| | |
|---|---|
| *A61P 29/00* | (2006.01) |
| *A61K 31/495* | (2006.01) |
| *A61K 9/00* | (2006.01) |
| *A61K 31/47* | (2006.01) |
| *A61K 31/4706* | (2006.01) |
| *A61K 31/496* | (2006.01) |
| *A61K 31/60* | (2006.01) |
| *A61K 31/612* | (2006.01) |
| *A61K 31/7088* | (2006.01) |
| *A61K 45/06* | (2006.01) |

(52) U.S. Cl.
CPC ............ *A61K 31/495* (2013.01); *A61K 9/0024* (2013.01); *A61K 31/47* (2013.01); *A61K 31/4706* (2013.01); *A61K 31/496* (2013.01); *A61K 31/60* (2013.01); *A61K 31/612* (2013.01); *A61K 31/7088* (2013.01); *A61K 45/06* (2013.01)

(58) Field of Classification Search
USPC ................... 424/85.6, 520, 86, 486, 9.1, 400; 436/86; 514/1, 2, 44, 165; 536/23.1, 536/24.5; 435/91.1, 91.31
See application file for complete search history.

(56) References Cited

U.S. PATENT DOCUMENTS

| | | | | |
|---|---|---|---|---|
| 3,773,929 | A * | 11/1973 | Huber et al. | ............... 424/94.4 |
| 5,763,422 | A * | 6/1998 | Lichtenberger et al. | ......... 514/78 |
| 2004/0127470 | A1 | 7/2004 | Masferrer | |
| 2005/0148554 | A1* | 7/2005 | Zhang et al. | ................. 514/159 |
| 2005/0158302 | A1* | 7/2005 | Faustman et al. | .......... 424/131.1 |
| 2005/0239733 | A1 | 10/2005 | Jurk et al. | |
| 2009/0053148 | A1 | 2/2009 | Kandimalla et al. | |
| 2009/0239831 | A1 | 9/2009 | Mehal et al. | |
| 2010/0016262 | A1 | 1/2010 | Mehal et al. | |
| 2011/0135602 | A1* | 6/2011 | Ivanov et al. | ................ 424/85.5 |
| 2011/0256130 | A1* | 10/2011 | Schultz et al. | ............. 424/133.1 |
| 2012/0115782 | A1 | 5/2012 | Mehal et al. | |
| 2013/0071458 | A1* | 3/2013 | Kanamathareddy et al. | . 424/405 |

FOREIGN PATENT DOCUMENTS

| | | |
|---|---|---|
| WO | 2009051840 A2 | 4/2009 |
| WO | 2010121128 A2 | 10/2010 |

OTHER PUBLICATIONS

Genovese, M.C., Western J. Med., vol. 167, pp. 149-158 (1997).*
Hunt et al., British Med. J., vol. 316, pp. 1328-1329 (1998).*
Tang et al., Molec. Med., vol. 5, pp. 351-358 (1999).*
Anderson, J.M., Cardiovasc. Pathol., vol. 2, No. 3 Supp., pp. 33S-41S (1993).*
Imaeda et al., J. Clin. Invest., vol. 119, No. 2, pp. 305-314 (Feb. 2009).*
Wang D et al., Oligodeoxyribonucleotide-Based Antagonists for Toll-Like Receptors 7 and 9; J. Med. Chem. 2009; 52:551-558.
Yu D et al., Modifications Incorporated in CpG Motifs of Oligodeoxynucleotides Lead to Antagonist Activity of Toll-like Receptors 7 and 9; J. Med. Chem. :5108-5114, 2009.
Imaeda AV, et al., Acetaminophen-induced hepatotoxicity in mice is dependent on Tlr9 and the Nalp3 inflammasome, J. Clin. Invest. 2009; 119:305-314.
Miura K, et al., Toll-Like Receptor 9 Promotes Steatohepatitis by Induction of Interleukin-1beta in Mice; Gastroenterology 2010; 139:3323-334. Epub Mar. 27, 2010.
Hundal, R.S. et al.; Mechanism by which high-dose aspirin improves glucose metabolism in type 2 diabetes. The Journal of Clinical Investigation May 2002; 109:1321-1326. doi:10.1172/JCI200214955.
Lee, W.M. 2007. Acetaminophen toxicity: changing perceptions on a social/medical issue. Hepatology 46:966-970.
Kaplowitz, N. 2004. Acetaminophen hepatotoxicity: what do we know, what don't we know, and what do we do next? Hepatology 40:23-26.
Liu, Z.X., Han, D., Gunawan, B., and Kaplowitz, N. 2006. Neutrophil depletion protects against murine acetaminophen hepatotoxicity. Hepatology 43:1220-1230.
Liu, Z.X., Govindarajan, S., and Kaplowitz, N. 2004. Innate immune system plays a critical role in determining the progression and severity of acetaminophen hepatotoxicity. Gastroenterology 127:1760-1774.
Cover, C., Liu, J., Farhood, A., Malle, E., Waalkes, M.P., Bajt, M.L., and Jaeschke, H. 2006. Pathophysiological role of the acute inflammatory response during acetaminophen hepatotoxicity. Toxicol Appl Pharmacol 216:98-107.

(Continued)

*Primary Examiner* — Jane Zara
(74) *Attorney, Agent, or Firm* — Henry D. Coleman

(57) ABSTRACT

The present invention relates, inter alia, to methods and compositions for regulating the host response to biomaterials, including inhibiting inflammation from and rejection of biomaterials using salicylate compounds and/or TLR7/TLR9 antagonists as described herein.

18 Claims, 9 Drawing Sheets

(56) References Cited

OTHER PUBLICATIONS

Fiorucci, S., Antonelli, E., Mencarelli, A., Palazzetti, B., Alvarez-Miller, L., Muscara, M., del Soldato, P., Sanpaolo, L., Wallace, J.L., and Morelli, A. 2002. A NO-releasing derivative of acetaminophen spares the liver by acting at several checkpoints in the Fas pathway. Br J Pharmacol 135:589-599.

Chen, C.J., Kono, H., Golenbock, D., Reed, G., Akira, S., and Rock, K.L. 2007. Identification of a key pathway required for the sterile inflammatory response triggered by dying cells. Nat Med 13:851-856.

Mariathasan, S., Newton, K., Monack, D.M., Vucic, D., French, D.M., Lee, W.P., Roose-Girma, M., Erickson, S., and Dixit, V.M. 2004. Differential activation of the inflammasome by caspase-1 adaptors ASC and Ipaf. Nature 430:213-218.

Martinon, F., Burns, K., and Tschopp, J. 2002. The inflammasome: a molecular platform triggering activation of inflammatory caspases and processing of proIL-beta. Mol Cell 10:417-426.

Ogura, Y., Sutterwala, F.S., and Flavell, R.A. 2006. The inflammasome: first line of the immune response to cell stress. Cell 126:659-662.

Vollmer, J. 2006. TLR9 in health and disease. Int Rev Immunol 25:155-181.

Lamphier, M.S., Sirois, C.M., Verma, A., Golenbock, D.T., and Latz, E. 2006. TLR9 and the recognition of self and non-self nucleic acids. Ann N Y Acad Sci 1082:31-43.

Enari, M., Sakahira, H., Yokoyama, H., Okawa, K, Iwamatsu, A., and Nagata, S. 1998. A caspase-activated DNase that degrades DNA during apoptosis, and its inhibitor ICAD. Nature 391:43-50.

Huck, S., Deveaud, E., Namane, A., and Zouali, M. 1999. Abnormal DNA methylation and deoxycytosine-deoxyguanine content in nucleosomes from lymphocytes undergoing apoptosis. Faseb J 13:1415-1422.

Lunec, J., Herbert, K., Blount, S., Griffiths, H.R., and Emery, P. 1994. 8-Hydroxydeoxyguanosine. A marker of oxidative DNA damage in systemic lupus erythematosus. FEBS Lett 348:131-138.

Rifkin, I.R., Leadbetter, E.A., Busconi, L., Viglianti, G., and Marshak-Rothstein, A. 2005. Toll-like receptors, endogenous ligands, and systemic autoimmune disease. Immunol Rev 204:27-42.

Mariathasan, S., and Monack, D.M. 2007. Inflammasome adaptors and sensors: intracellular regulators of infection and inflammation. Nat Rev Immunol 7:31.40.

Barrat, F.J., Meeker, T., Chan, J.H., Guiducci, C., and Coffman, R.L. 2007. Treatment of lupus-prone mice with a dual inhibitor of TLR7 and TLR9 leads to reduction of autoantibody production and amelioration of disease symptoms. Eur J Immunol 37:3582-3586.

Barrat, F.J., Meeker, T., Gregorio, J., Chan, J.H., Uematsu, S., Akira, S., Chang, B., Duramad, O., and Coffman, R.L. 2005. Nucleic acids of mammalian origin can act as endogenous ligands for Toll-like receptors and may promote systemic lupus erythematosus. J Exp Med 202:1131-1139.

Dinarello, C.A. 2007. Interleukin-18 and the pathogenesis of inflammatory diseases. Semin Nephrol 27:98-114.

Pirhonen, J., Sareneva, T., Kurimoto, M., Julkunen, I., and Matikainen, S. 1999. Virus infection activates IL-1 beta and IL-18 production in human macrophages by a caspase-1-dependent pathway. J Immunol 162:7322-7329.

Kalina, U., Koyama, N., Hosoda, T., Nuernberger, H., Sato, K., Hoelzer, D., Herweck, F., Manigold, T., Singer, M.V., Rossol, S., et al. 2002. Enhanced production of IL-18 in butyrate-treated intestinal epithelium by stimulation of the proximal promoter region. Eur J Immunol 32:2635-2643.

Watanabe, A., Hashmi, A., Gomes, D.A., Town, T., Badou, A., Flavell, R.A., and Mehal, W.Z. 2007. Apoptotic hepatocyte DNA inhibits hepatic stellate cell chemotaxis via toll-like receptor 9. Hepatology 46:1509-1518.

Martin-Armas, M., Simon-Santamaria, J., Pettersen, I., Moens, U., Smedsrod, B., and Sveinbjornsson, B. 2006. Toll-like receptor 9 (TLR9) is present in murine liver sinusoidal endothelial cells (LSECs) and mediates the effect of CpG-oligonucleotides. J Hepatol 44:939-946.

Traggiai, E., Chicha, L., Mazzucchelli, L., Bronz, L., Piffaretti, J.C., Lanzavecchia, A., and Manz, M.G. 2004. Development of a human adaptive immune system in cord blood cell-transplanted mice. Science 304:104-107.

Puren, A.J., Fantuzzi, G., and Dinarello, C.A. 1999. Gene expression, synthesis, and secretion of interleukin 18 and interleukin 1beta are differentially regulated in human blood mononuclear cells and mouse spleen cells. Proc Natl Acad Sci U S A 96:2256-2261.

Martinon, F., Petrilli, V., Mayor, A., Tardivel, A., and Tschopp, J. 2006. Gout-associated uric acid crystals activate the NALP3 inflammasome. Nature 440:237-241.

Wu, K.K., Liou, J.Y., and Cieslik, K. 2005. Transcriptional Control of COX-2 via C/EBPbeta. Arterioscler Thromb Vasc Biol 25:679-685.

Reilly, T.P., Brady, J.N., Marchick, M.R., Bourdi, M., George, J.W., Radonovich, M.F., Pise-Masison, C.A., and Pohl, L.R. 2001. A protective role for cyclooxygenase-2 in drug-induced liver injury in mice. Chem Res Toxicol 14:1620-1628.

Wu, K.K. 2003. Aspirin and other cyclooxygenase inhibitors: new therapeutic insights. Semin Vasc Med 3:107-112.

Viglianti, G.A., Lau, C.M., Hanley, T.M., Miko, B.A., Shlomchik, M.J., and Marshak-Rothstein, A. 2003. Activation of autoreactive B cells by CpG dsDNA. Immunity 19:837-847.

Tsutsui, H., Matsui, K., Okamura, H., and Nakanishi, K. 2000. Pathophysiological roles of interleukin-18 in inflammatory liver diseases. Immunol Rev 174:192-209.

Pomerantz, B.J., Reznikov, L.L., Harken, A.H., and Dinarello, C.A. 2001. Inhibition of caspase 1 reduces human myocardial ischemic dysfunction via inhibition of IL-18 and IL-1beta. Proc Natl Acad Sci U S A 98:2871-2876.

Akahoshi, T., Murakami, Y., and Kitasato, H. 2007. Recent advances in crystal-induced acute inflammation. Curr Opin Rheumatol 19:146-150.

Duncan, J.A., Bergstralh, D.T., Wang, Y., Willingham, S.B., Ye, Z., Zimmermann, A.G., and Ting, J.P. 2007. Cryopyrin/NALP3 binds ATP/dATP, is an ATPase, and requires ATP binding to mediate inflammatory signaling. Proc Natl Acad Sci U S A 104:8041-8046.

Tsujimoto, H., Ono, S., Matsumoto, A., Kawabata, T., Kinoshita, M., Majima, T., Hiraki, S., Seki, S., Moldawer, L.L., and Mochizuki, H. 2006. A critical role of CpG motifs in a murine peritonitis model by their binding to highly expressed toll-like receptor-9 on liver NKT cells. J Hepatol 45:836-843.

Whitehouse, L.W., Paul, C.J., and Thomas, B.H. 1976. Effect of acetylsalicylic acid on a toxic dose of acetaminophen in the mouse. Toxicol Appl Pharmacol 38:571-582.

De Vries, J., De Jong, J., Lock, F.M., Van Bree, L., Mullink, H., and Veldhuizen, R.W. 1984. Protection against paracetamol-induced hepatotoxicity by acetylsalicylic acid in rats. Toxicology 30:297-304.

Kuida, K., Lippke, J.A., Ku, G., Harding, M.W., Livingston, D.J., Su, M.S., and Flavell, R.A. 1995. Altered cytokine export and apoptosis in mice deficient in interleukin-1 beta converting enzyme. Science 267:2000-2003.

Sutterwala, F.S., Ogura, Y., Szczepanik, M., Lara-Tejero, M., Lichtenberger, G.S., Grant, E.P., Bertin, J., Coyle, A.J., Galan, J.E., Askenase, P.W., et al. 2006. Critical role for NALP3/CIAS1/Cryopyrin in innate and adaptive immunity through its regulation of caspase-1. Immunity 24:317-327.

Schmassmann, A., Zoidl, G., Peskar, B.M., Waser, B., Schmassmann-Suhijar, D., Gebbers, J.O., and Reubi, J.C. 2006. Role of the different isoforms of cyclooxygenase and nitric oxide synthase during gastric ulcer healing in cyclooxygenase-1 and -2 knockout mice. Am J Physiol Gastrointest Liver Physiol 290:G747-756.

Sjoholm A et al.; Inflammation and the etiology of type 2 diabetes. Diabetes/metabolism Research and Reviews 2006; 22:4-10.

Trujillo-Murillo K et al.; Acetylsaliclic Aacid Inhibits Hepatitis C Virus RNA and Protein Expression Through Cyclooxygenase 2 Signaling Pathways. Hepatology 2008; 47:14262-14272.

Denda A et al.; Prevention by acetylsalicylic acid of liver cirrhosis and carcinogenesis as well as generations of 8-hydroxyguanosine and thiobarbituric acid-reactible substances caused by a choline-deficient, L-amino acid-denied diet in rats. Carcinogenesis. 1994; 15:1279-1283.

(56) References Cited

OTHER PUBLICATIONS

Imaeda AB et al.; Acetaminophen-induced hepatotoxicity in mice is dependent on Tlr9 and the Nalp3 inflammasome. J. Clin. Invest. 2009, 119:305-314.

Assy N et al.; The Beneficial Effect of Aspirin and Enoxaparin on Fibrosis Progression and Regenerative Activity in a Rat Model of Cirrhosis. Dig Dis Sci 2007; 52:1187-1193.

Sahasrabuddhe VV et al.; Nonsteroidal Anti-inflammatory Drug Use, Chronic Liver Disease, and Hepatocellular Carcinoma. J Natl Cancer Inst Nov. 28, 2012; pp. 1-7.

Kimura et al.; Metallothionein acts as a cytoprotectant against doxorubicin toxicity. JPET 2000; 292: 299-302.

Krysko DV et al.; TLR-2 and TLR-9 are sensors of apoptosis in a mouse model of doxorubicin-induced acute inflammation. Cell Death and Differentiation 2001; 18:1316-1325.

Kaplowitz N et al.; Effect of Salcylates and Phenobarbital on Hepatic Glutathione in the Rat. J Pharm and Exp Ther 1979; 212:240-245.

Han D et al.; Mechanisms of Liver Injury. III. Role of glutathione redox status in liver injury. Am J Physiol Gastrointest Liver Physiol 2006; 291: G1-G7.

Piemonte F et al.; protein glutathionylation increases in the liver of patients with non-alcoholic fatty liver disease. Journal of Gastroenterology and Hepatology 2008; 23: e457-e464. Epub Aug. 6, 2007.

Encke et al.; Immunosuppression and modulation in liver transplantation. Nephrol Dial Transplant 2004; 19(Suppl 4): iv22-iv25.

Giboney et al.; Mildly Elevated Live Transaminase Levels in the Asymptomatic Patient. Am Fam Physician 2005; 71: 1105-10.

Kaneda et al.; Inflammatory Liver Steatosis Caused by IL-12 and IL-18. Journal of Interferon & Cytokine Research 2003; 23: 155-162.

Fox JM; Kombinationsarzneimittel aus Paracetamol plus Acetylsalicylsaure: Nutzen und Risken [Combination analgesics consisting of paracetamol plus acetylsalicylic acid: Benefits and Risks] Schmerz Nov. 1, 1995; 9:273-285.

Grennan DM et al.; The Aspirin-Ibuprofen Interaction in Rheumatoid Arthritis. Br J Clin Pharmac Jan. 1, 1979; pp. 497-503.

Does Aspirin Harm the Liver? The Lancet Apr. 1, 1974 ; 303:667 Abstract XP055077832.

Imaeda AB et al.; 467 Aspirin Blocks Acetaminophen Induced Hepatotoxicity and Mortality in Mice-Dependent on the ACS/Caspase-1 Inflammasome. Gastroenterology Apr. 1, 2008; 134:A-767.

Database WPI Week 200347; Thompson Scientific, London, GB; AN 2003-500900; XP002712530, & KR 2002 0007566 A (Samjin Pharm Co Ltd) Jan. 29, 2002. Abstract.

Database Biosis [Online] Biosciences Information Service, Philadelphia, PA, US Oct. 2004, Carroll CL et al; Better medication adherence results in greater improvement in severity of psoriasis. XP02712346, Database accession No. PREV200500038983. Abstract. & Carroll CL et al.Better medication adherence results in greater improvement in severity ofpsoriasis. British Journal of Dermatology Oct. 2004; 151:895-897.

Database Embase [Online]; Elsevier Science Publishers, Amsterdam, NL; 1982, Shaw JFL: Combined effects of cyclosporin A and sodium salicylate upon survival of rat heart allografts. XP002712347, Database accession No. EMB-1982249805 *abstract* & Shaw JFL; Combined effects of cyclosporin A and sodium salicylate upon survival of rat heart allografts. IRCS Medical Science 1982 GB 1982; 10:827.

Miura K et al.; Toll-Like Receptor 9 Promotes Steatohepatitis by Induction of Interleukin-1beta in mice. Gastroenterology 2010; 139:323-334.

\* cited by examiner

FIGURE 1
Mesh
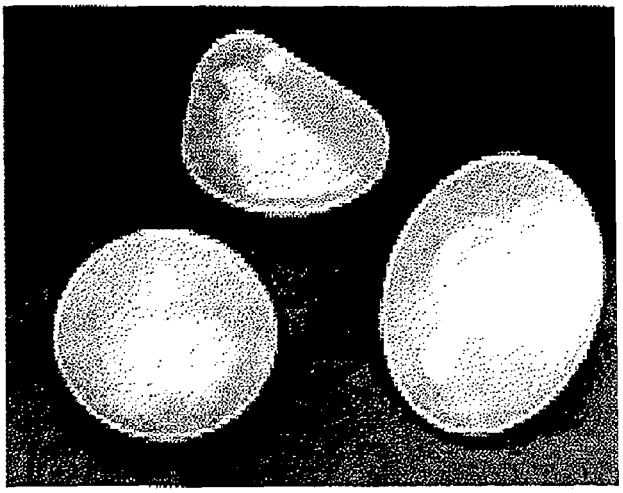
Breast Implant
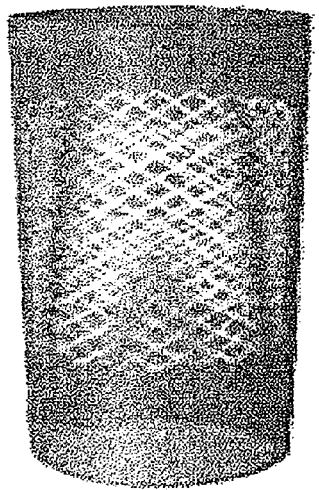
Vascular Stent
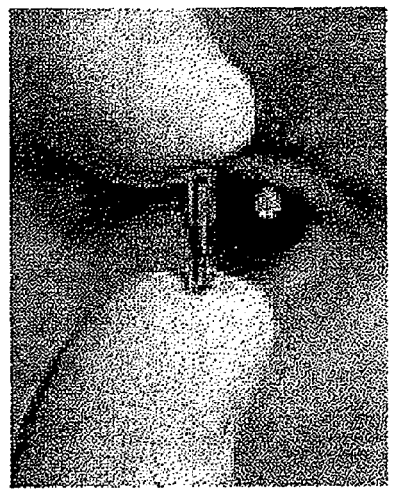
Glucose Sensor Continuous aspirin in drinking water reduces the thickness of the foreign body reaction in normal mice

FIGURE 8

| Strand | (Sequence 5'–3' 21-mer) | SEQ ID No: |
|---|---|---|
| S | AGAUCACCCUCCUUAAAUAUU | 1 |
| S | AGAUCACCCUCCUUAAAUAUU | 2 |
| AS | UAUUUAAGGAGGGUGAUCUUU | 3 |
| AS | UAUUUAGGAGGGUGAUCUUU | 4 |
| AS | UAUUUAAGGAGGGUGAUCUUU | 7 |
| S | AGACCUACCUCCGGAUCAAUU | 8 |
| S | AGACCUACCUCCGGAUCAAUU | 9 |
| AS | UUGAUCCGGAGGUAGGUCUUU | 10 |
| AS | UUGAUCCGGAGGUAGGUCUUU | 11 |
| AS | UUGAUCCGGAGGUAGGUCUUU | 12 |
| S | CUGAAGACCUGAAGACAAUdTdT | 13 |
| S | CUGAAGACCUGAAGACAAUdTdT | 14 |
| AS | AUUGUCUUCAGGUCUUCAGdTdT | 15 |
| AS | AUUGUCUUCAGGUCUUCAGdTdT | 16 |
| S | GAUUAUGUCCGGUUAUGUAUU | 17 |
| AS | UACAUAACCGGACAUAAUCUU | 18 |

Bold underlined indicates 2'0-Methylation of those Nucleotides for the 21 MER sequences

FIGURE 9

| SEQUENCE | SEQ. ID. NO: |
|---|---|
| TCCTGGCGGGGAAGT | 26 |
| TCCTGGAGGGGAAGT | 27 |
| TCCTGGATGGGAAGT | 28 |
| CCTGGATGGGAATTCCCATCCAGG | 29 |
| TTCCCATCCAGGCCTGGATGGGAA | 30 |
| CCTGGATGGGAACTTACCGCTGCA | 31 |
| GGGGGGGGGGGGGGGGGGGG | 32 |
| TTAGGGTTAGGGTTAGGGTTAGGG | 33 |
| TGACTGTGAAGGTTAGAGATGA | 34 |
| CTCCTATTGGGGGTTTCCTAT | 35 |
| TCCTGGAGGGGTTGT | 36 |
| TGCTTGCAAGCTTGCAAGCA | 37 |
| TGCTCCTGGAGGGGTTGT | 38 |

COMPOSITIONS AND METHODS FOR INHIBITING INFLAMMATION FROM AND REJECTION OF BIOMATERIALS AND OTHER METHODS

RELATED APPLICATIONS

This application claims the benefit of priority of and is a United States national phase application of International Patent Application No. PCT/US2010/050544 of International Filing Date 28 Sep. 2010, which is entitled "COMPOSITIONS AND METHODS FOR INHIBITING INFLAMMATION FROM AND REJECTION OF BIOMATERIALS AND OTHER METHODS", which claims the benefit of priority from two United States provisional patent applications, United States provisional application serial number U.S. 61/277,798, filed Sep. 29, 2009 entitled "Therapeutic regulation of the host response to biomaterials by inhibition of inflammasome pathways" and provisional application U.S. 61/281,823, filed Nov. 23, 2009, entitled "Compositions and Methods for Treating or Inhibiting Liver Injury, Related Conditions and For Inhibiting Inflammation from and Rejection of Biomaterials", all three of which applications are incorporated by reference in their entirety herein.

GOVERNMENT SUPPORT

This invention was made with government support under grant number 1 R01 DK076674-01A2 awarded by the National Institutes of Health. Consequently, the government has certain rights in the invention.

FIELD OF THE INVENTION

The present invention relates to methods and compositions for regulating the host response to biomaterials, including inhibiting inflammation from and rejection of biomaterials using salicylate compounds and/or TLR7/TLR9 antagonists as described herein.

BACKGROUND OF THE INVENTION

The insertion of a foreign inert substance into the body of a patient or subject results in a series of biochemical and cellular responses by the body which is termed the foreign body reaction. The clinical consequences of foreign body reaction include, for example, deposition of cells and collagenous matrix around the device; pain and swelling at the site of the biomaterial; scarring at the site of the biomaterials, limited function of the biomaterial and/or medical device. Currently, there are no effective therapeutic strategies which can limit foreign body reaction, although limited improvement (and numerous side effectis) has been seen with the administration of steroids.

Currently there are 8.7 million breast implantations each year with a complication rate, due to foreign body reaction, of approximately 5.3%. There are approximately 200,000 breast reconstruction surgeries a year with a complication rate of approximately 25%. There are approximately 175,000 coronary stents introduced into coronary vessels of patients every year, with a re-stenosis rate of approximately 15%. Neointimal tissue builds up inside the stent triggered by the inflammatory response (a type of foreign body reaction). Various long-term implantable sensors, which produce foreign body reaction resulting in device failure of approximately 100% and other devices are in clinical trials. Limitations on their use relates to the frequent occurrence of foreign body reaction (FBR) with the introduction of these devices into a patient.

Thus, there is a very large unmet need in a very large clinical area which is addressed by the present invention. The present inventors have demonstrated a role for the cellular machinery involved in sterile inflammation in a range of disease models and biological processes. These include sterile liver injury by acetaminophen (APAP), pancreatitis and the foreign body reaction to biomaterials. Important components of this machinery are membrane receptors which can detect cellular perturbation and cellular death. The present inventors have identified that TLR7 and TLR9 serve an important role in vivo by detecting cellular death. TLR7 and TLR9 serve this role by undergoing activation in response to endogenous cellular materials including nucleic acids. The inventors have shown that TLR7 and TLR9 results in initiation of a sterile inflammatory response to a wide range of clinically important conditions, including drug induced liver injury (for example, APAP among numerous others), non-alcoholic steatohepatitis, alcoholic steatohepatitis, and even hepatitis caused by viral infections, including hepatitis B and C. TLR7 and TLR9 also play an important role in a wide range of other types of inflammatory diseases, including pancreatitis and the inflammation caused by foreign body reaction to biomaterials as described above.

BRIEF DESCRIPTION OF THE FIGURES

FIG. 1 shows that the present invention is useful for reducing foreign body reaction to a number of biomaterials. In this figure, a number of medical devices are shown including cell/tissue support mesh, breast implants, vascular stens and glucose sensors.

FIG. 4A shows Less up-regulation of inflammatory pro-cytokine mRNA in whole liver tissue of wild-type mice treated with a TLR9 antagonist. Data from 12 hours after APAP. FIG. 4B shows less increases in serum ALT of wild-type mice treated with a TLR9 antagonist. Data from 12 hours after APAP administration. FIG. 4C shows significantly improved survival in wild-type mice treated with a combined TLR7 and TLR9 antagonist. Data over 3 days. FIG. 4D shows less increases in serum SLT of wild-type mice treated with a TLR 7/9 antagonist. Data from 12 hours after APAP. *P<0.05.

FIG. 5A shows H & E staining of pancreas from wild-type mouse given cerulin without TLR 7/9 antagonist. FIG. 5B shows wild-type mouse given cerulin without TLR. FIG. 5C shows a summary of histological scoring which grades edema, inflammation and cell death, showing less overall injury when a TLR7/9 antagonist is given along with cerulin. FIGS. 5D & 5E show staining for neutrophils showing less neutrophil infiltrate in the pancreas with TLR 7/9 antagonist treatment. FIG. 5F shows the quantitation of reduced neutrophil infiltrate with TLR 7/9 antagonist treatment. *P<0.05.

FIG. 7 shows that there is a significant reduction in the thickness of the foreign body reaction capsule on the side of the muscle and on the side of the skin. * indicates P<0.05 compared to no ASA. All mice were wild-type. CT=control mouse without aspirin, Asp=mouse on aspirin in drinking water.

FIGS. 8 and 9 show representative oligonucleotide compounds which are TLR7 and/or 9 antagonists.

BRIEF DESCRIPTION OF THE INVENTION

Figure 2:
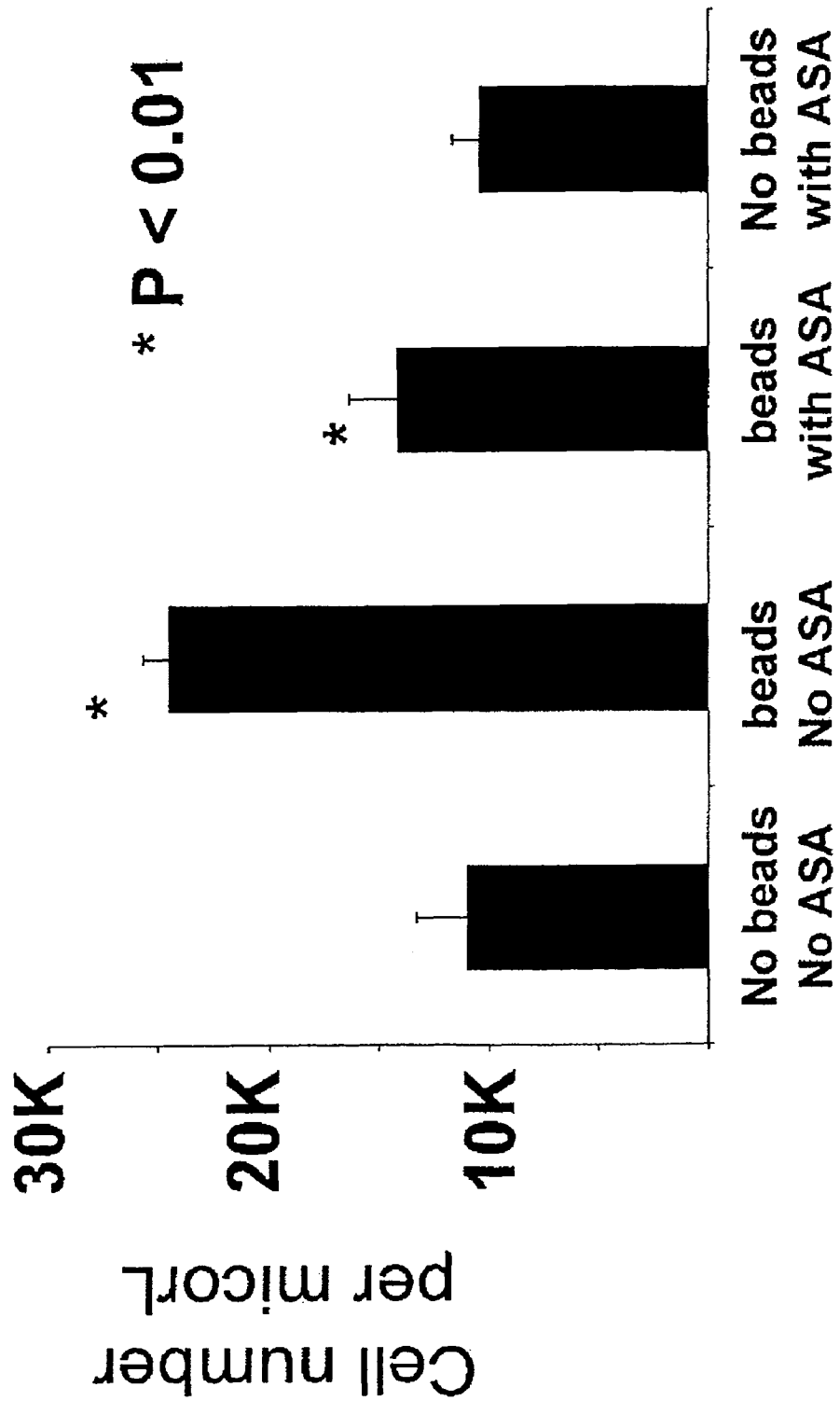
FIG. 2 that the continuous administration of aspirin limits the foreign body reaction to polystyrene beads in the abdominal cavity of mice at 24 hours. The cellular infiltrate at 24 hours was composed mostly of immune cells, in particular neutrophils and macrophages. Note that although the number of cells was significantly reduced by the administration of aspirin, the composition of the cellular infiltrate was not significantly altered by the aspirin.

The present invention relates to the discovery that TLR 7/9 antagonists and their pharmaceutically acceptable salts and separately, salicylic acid and related compounds and their pharmaceutically acceptable salts may be used to inhibit or reduce inflammation and related secondary effects from the use of implants and related implanted biomaterials. In the present application, an effective amount of at least one TLR7 and/or TLR9 antagonist and/or a salicylate compound as otherwise disclosed herein may be administered to a patient or subject who is exhibiting inflammation and/or other related secondary effects associated with the use of implants and related implanted biomaterials in order to inhibit and/or alleviate the inflammation and/or related secondary effects. In a further aspect of the invention, compounds according to the present invention may be administered to a patient or subject who will have an implant or other biomaterial implanted in order to inhibit or reduce the likelihood of inflammation and/or other related secondary effects that will occur in the patient after the introduction of the biomaterial.

The present method is applicable and adaptable to virtually any biomaterial and medical device which has been introduced into a patient and produces inflammation or a related secondary effect (side effect) from the introduction of the biomaterial into the patient or subject. The present method is useful with a large number of biomaterials which are used in implants, sutures, medical devices, materials for introduction and/or supporting cellular materials and related tissues, etc. which produce or can produce inflammation or related side effect/secondary effect in patient or subject in the biomaterial is introduced. The present invention may be used to improve the function of biomaterials and/or reduce the likelihood that biomaterials and medical devices will have to replaced. The present invention results in the increase of the time period of residence (enhance residence time) of biomaterials and medical devices within the patient or subject before the biomaterials or medical device needs to be replaced. In addition, the present method is useful for reducing other secondary effects from inflammation related to biomaterials which are introduced into a patient or subject, including the deposition of cells (e.g. neutrophils, macrophages), pain and swelling at the site of the biomaterial, scarring and tenderness at the site of the biomaterial and infections which occur due to bacterial biofilm formation, among others. The present invention also may be used to increase the effectiveness and residence time of biomaterials and medical devices such that the biomaterials and/or medical devices exhibit increased therapeutic effectiveness. Pursuant to the present invention, in some cases, biomaterials and/or medical devices which have, heretofore, been considered of limited utility or inapplicable to provide clinically relevant therapies because of significant inflammation and other secondary effects (reducing residence time or rejection) associated with the introduction of the biomaterials and/or medical devices are now clinically relevant, an important factor in enhancing therapies for a number of disease states and/or conditions.

The present invention also relates to the use of TLR7/9 antagonists for inhibiting or treating liver toxicity, for example to reduce hepatotoxicity associated with drug therapy, represents an additional aspect of the present invention. The present invention results in a patient being protected from acute and chronic liver toxicity and/or injury associated with the administration of hepatotoxic bioactive agents or a disease state or disease which can produce liver toxicity and/or liver injury. The present invention also relates to a method for reducing the likelihood of and/or inhibiting inflammation of the pancreas (pancreatitis).

Methods of reducing the likelihood of liver injury occurring from or secondary to a variety of etiologies especially including hepatitis (all forms, including viral hepatitis), non-alcoholic fatty liver diseases (NAFLD) in a patient at risk for same, including non-alcoholic steatohepatitis (NASH), or for treating NAFLD or NASH including primary NASH, NASH secondary to liver transplantation (NASH post-liver transplantation), preservation injury of donated organs, acute and chronic liver transplant rejection and metabolic conditions including, for example, Wilson's disease, hemochromatosis, and alpha one antitrypsin deficiency represent alternative aspects of the present invention. As a consequence of the actions of the TLR 7/9 antagonist compounds of the present invention in inhibiting or reducing the likelihood of liver injury, the following complications are inhibited and/or reduced: liver failure, cirrhosis (which also may be treated using the present invention), portal hypertension, ascites, variceal bleeding, encephalopathy, depression, malaise, renal disease, arthritis, portal vein thrombosis and budd chiari.

In addition, the present invention relates to a method of reducing liver damage incidental to physical or chemical trauma to the liver, including acetaminophen-induced or drug induced acute liver trauma of a patient comprising administering an effective amount of a compound as otherwise described herein to a patient in need to reduce such liver damage.

The present invention relates to the discovery that a TLR 7/9 antagonist as otherwise disclosed herein and/or a salicylate compound according to the structure:

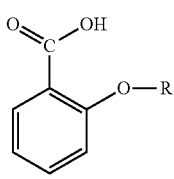

Where R is H or a $C_2$-$C_{10}$ acyl group (preferably, H or an acetyl other straight-chained alkyl group), or a pharmaceutically acceptable salt thereof, may be used in combination with a bioactive agent which produces significant hepatotoxicity ("a hepatotoxicity inducing bioactive agent") in the absence of said salicylate compound to substantially reduce said hepatotoxicity. In preferred aspects of the invention, the salicylate compound is acetylsalicylic acid (aspirin, R=$C_2$ acyl or acetyl group) or a pharmaceutically acceptable salt thereof.

Thus, in one aspect, the present invention relates to pharmaceutical compositions which comprise an effective amount of a TLR 7/9 antagonist and/or salicylate compound as set forth above, in combination with at least one bioactive agent which produces hepatotoxicity as a side effect, optionally in combination with a pharmaceutically acceptable carrier, additive or excipient. In certain aspects, the pharmaceutical composition includes a high dose effective amount of a bioactive agent in combination with the TLR 7/9 antagonist and/or salicylate. In other aspects, the invention relates to embodiments wherein a TLR 7/9 antagonist or salicylate compound as described above is formulated in combination with a type II diabetes treating agent selected from the group consisting of metformin, glibenclamide, gliclazide, rosiglitazone, pioglitazone, troglitazone, acarbose, miglitol, nateglinide, repaglinide, exenatide, sitagliptin, pramlintide and mixtures thereof and/or an immune suppressive agent selected from the group consisting of cyclosporine, tacrolimus, prednisone, azathioprine, mycophenolate mofetil, daclizumab, basiliximab and mixtures thereof, all in effective amounts, optionally in combination with a pharmaceutically acceptable carrier, additive or excipient.

In another aspect, the present invention relates to a method for reducing hepatotoxicity secondary to the administration of bioactive agent which produces hepatotoxicity as a secondary or side effect, the method comprising coadministering an effective amount of at least one TLR 7/9 antagonist and/or salicylate compound as described above in combination with said bioactive.

The present method is applicable and adaptable to a large number of heptatoxicity inducing bioactive agents which produce hepatotoxicity and limit their usefulness because of that hepatotoxicity. The present invention may be used to increase the effectiveness of such bioactive agents (for example by increasing an agent's therapeutic index and/or increasing the dose which may be administered to a patient). Pursuant to the present invention, in some cases, bioactive agents which have, heretofore, been considered of limited utility as clinically relevant therapies because of significant hepatotoxicity associated with the administration of these agents are now clinically relevant, an important factor in enhancing the armamentarium against a number of disease states and conditions, especially including HIV infections, among others.

The present invention is also directed to methods of inhibiting or reducing the likelihood of liver injury in a patient at risk for same occurring from or secondary to a variety of etiologies especially including hepatitis (all forms, especially including hepatitis viral), non-alcoholic fatty liver diseases (NAFLD), including non-alcoholic steatohepatitis (NASH), NAFLD or NASH including primary NASH, NASH secondary to liver transplantation (NASH post-liver transplantation), preservation injury of donated organs, acute and chronic liver transplant rejection and metabolic conditions including, for example, Wilson's disease, hemochromatosis, and alpha one antitrypsin deficiency represent alternative aspects of the present invention. In this method, an effective amount of a compound (TLR 7/9 antagonist and/or salicylate compound) according to the present invention is administered to a patient at risk for liver injury as described above in order to inhibit or reduce the likelihood of liver injury as described above. As a consequence of the actions of compounds according to the present invention in reducing and/or inhibiting liver injury, certain complications of liver injury may be reduced including, for example, liver failure, liver shock, obstructive jaundice, cirrhosis, including primary biliary cirrhosis, primary sclerosing cholangitis, portal hypertension, ascites, variceal bleeding, encephalopathy, depression, malaise, renal disease, arthritis, portal vein thrombosis, and budd chiari.

The present invention is also directed to treating liver injury and/or reducing the likelihood of further liver injury associated with or occurring directly from or secondary to a variety of etiologies especially including hepatitis (all forms), cirrhosis (all types), non-alcoholic fatty liver diseases (NAFLD), including non-alcoholic steatohepatitis (NASH), NAFLD or NASH including primary NASH, NASH secondary to liver transplantation (NASH post-liver transplantation), preservation injury of donated organs, acute and chronic liver transplant rejection and metabolic conditions including, for example, Wilson's disease, hemochromatosis, and alpha one antitrypsin deficiency. In this method, an effective amount of a salicylate compound according to the present invention is administered to a patient with liver injury and/or at risk for further liver injury as described above in order to treat, inhibit or reduce the likelihood of liver injury which occurs directly as a consequence of or secondary to one or more of the disease states and/or conditions as described above. As a consequence of the treatment methods described above, the occurrence and/or severity of one or more of the following conditions will be substantially reduced: liver failure, liver shock, obstructive jaundice, primary biliary cirrhosis, primary sclerosing cholangitis, portal hypertension, ascites, variceal bleeding, encephalopathy, depression, malaise, renal disease, arthritis, portal vein thrombosis and budd chiari.

The present invention is also directed to methods of treating hepatitis (all types, including non-alcoholic steatohepatitis (NASH)), cirrhosis (all types), fatty liver disease, including non-alcoholic fatty liver disease (NAFLD), including cirrhosis in a patient at risk, primary NASH or NASH secondary to liver transplantation, by administering an effective amount of a salicyclic acid compound as otherwise described hereinabove to said patient. In this aspect of the present invention, a method for treating NAFLD, NASH including primary NASH, cirrhosis and/or NASH secondary to liver transplantation (NASH post-liver transplantation) comprises administering to a patient in need thereof an effective amount of a salicylic acid compound as otherwise disclosed herein, optionally in combination with a carrier, additive or excipient. In treating the above disease states and/or conditions there is an inhibition or a reduction in the likelihood of liver injury or that one or more of the following conditions will occur in the treated patient: liver failure, portal hypertension, ascites, variceal bleeding, encephalopathy, depression, malaise, renal disease, arthritis, portal vein thrombosis and/or budd-chiari.

In certain embodiments related to the treatment of liver injury, NAFLD, NASH or cirrhosis which occurs secondary to a liver transplant, including acute and chronic transplant rejection, compounds according to the present invention may be coadministered to the transplant patient with an effective amount at least one immune suppressive agent selected from the group consisting of Sandimmune (cyclosporine), Neoral (cyclosporine), Prograf (tacrolimus), prednisone, Imuran (azathioprine), Cellcept (mycophenolate mofetil), Zenapax (daclizumab), or Simulect (basiliximab). In other alternative embodiments, the salicylate may be administered to a patient where applicable (in those conditions such as NAFLD, NASH, etc. which occur as a consequence of metabolic syndrome and/or type II diabetes) in combination with an effective amount of one or more agents which are used to treat type II diabetes or metabolic syndrome including metformin, glibenclamide, gliclazide, rosiglitazone, pioglitazone, troglitazone, acarbose, miglitol, nateglinide, repaglinide, exenatide, sitagliptin, pramlintide and mixtures thereof.

Certain embodiments of the present invention relate to the treatment of hepatitis (alcoholic and non-alcoholic), which occurs as a consequence of infections (viral and non-viral), drugs, ischemia, toxins, pregnancy, alcohol, toxins, autoimmune conditions (systemic lupus erythematosus) and metabolic conditions, including Wilson's disease, hemochromatosis and alpha one antitrypsin deficiency. Hepatitis which may be treated according to the present invention includes hepatitis which occurs as a consequence of infectious disease, especially including a viral infection such as a hepatitis A, B, C, D or E viral infection, or hepatitis which occurs as a consequence of a cytomegalovirus, Epstein-Barr, yellow fever, mumps virus, rubella virus, herpes simplex virus, or adenovirus infection or a non-viral selection including an infection from toxoplasma, leptospira, Q fever or Rocky Mountain Spotted Fever. In this embodiment, TLR7 and/or TLR 9 antagonists and/or salicylate compounds according to the present invention are administered in effective amounts to a patient with a viral hepatitis infection in order to inhibit, treat or reduce the likelihood of liver injury which occurs as a consequence of that viral or non-viral infection. Compounds according to the present invention may be administered alone or in combination with an effective amount of an anti-hepatitis infectious agent, such as an anti-viral agent, including Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof for hepatitis B infections and BILN 2061, ribavirin, interferon, NM 283, VX-950 (telaprevir), SCH 50304, TMC435, VX-500, BX-813, SCHSO3034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, VCH-222, PHX1766, SP-30 and mixtures thereof for hepatitis C infections. In an additional aspect of the invention, additional pharmaceutical compositions especially useful for treating hepatitis from viral infections, in particular, hepatitis b or hepatitis C infections comprise an effective amount of at least TLR 7 and/or 9 antagonist and/or at least one salicylate as disclosed herein in combination with at least one agent selected from the group consisting of hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof for hepatitis B infections and BILN 2061, ribavirin, interferon, NM 283, VX-950 (telaprevir), SCH 50304, TMC435, VX-500, BX-813, SCH503034 (boceprevir), R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, VCH-222, PHX1766, SP-30 and mixtures thereof, in combination with a pharmaceutically acceptable carrier, additive or excipient.

The present invention also relates to a method of inhibiting or down regulating sterile inflammation of the liver in a patient comprising administering en effective amount of at least one compound as otherwise disclosed herein to a patient in need thereof, optionally in combination with a pharmaceutically acceptable carrier additive or excipient and further optionally in combination with a type II diabetes treating agent and/or an immune suppressive agent as otherwise described herein. This method reduces the likelihood that sterile inflammation in the liver of patient will progress into NAFLD, NASH or cirrhosis in the treated patient.

Other aspects of the invention relate to a method for reducing liver damage to a patient who has been subjected to physical or chemical trauma, especially acute physical or chemical trauma including acetaminophen-induced acute liver trauma comprising administering to said patient an effective amount of a TLR7 and/or 9 antagonist and/or a salicylate as otherwise described herein.

Another aspect of the invention relates to methods for the preservation (against injury) of a liver after removal of the liver from a transplant donor and prior to transplantation in a patient, the method comprising exposing said liver after said removal and prior to transplantation to an effective amount of a TLR7 and/or 9 antagonist and/or a salicylate compound as described above, optionally in combination with a pharmaceutically acceptable carrier, additive or excipient. In certain aspects of the liver preservation method, the salicylate is in solution (preferably at a temperature below room temperature) and in further aspects of the invention, the liver is exposed to the solution and the liver and solution are frozen, including cryopreserved optionally in combination with a cryopreservation agent.

Other aspects of the invention are as otherwise described herein.

DETAILED DESCRIPTION OF THE INVENTION

The following terms shall be used to describe the present invention. In instances where a term is not specifically defined herein, the term shall be accorded its meaning, within the context of its use, as understood by those of ordinary skill in the art.

The term "compound" shall mean any specific compound which is disclosed within this specification and typically means a TLR7 and/or TLR9 antagonist or a salicylate, salicylate ester or a pharmaceutically acceptable salt thereof, or a bioactive agent or drug as otherwise described herein, including pharmaceutically acceptable salts thereof, generally a drug. Compounds are included in amounts effective to produce an intended physiological effect, and in many, but not all instances, may cause significant hepatotoxicity to a patient as a side or secondary effect of administering the drug to the patient. Certain other compounds may be used to treat secondary conditions such as type II diabetes or to suppress the immune system in liver transplant patients, or to treat viral infections directly (e.g., hepatitis B and/or C) in order to reduce the likelihood of a condition occurring or to advance therapies. Pharmaceutically acceptable salts are also compounds for use in the present invention.

The term "patient" or "subject" is used as it is generally understood by those of ordinary skill in the art and refers to an animal, preferably a mammal, even more preferably a human, in need of treatment or therapy to which compounds according to the present invention are administered in order to treat a condition or disease state treatable using compounds according to the present invention. Depending upon the disease or condition treated the term patient refers to the animal treated for that disease within context.

The term "effective" when used in context, shall mean any amount of a compound or component which is used to produce an intended result within the context of its use, which may be short-term or long-term. In the case of bioactive agents (i.e., compounds other than TLR7 and/or 9 antagonists and/or salicylate compounds) according to the present invention, the term effective generally refers to a therapeutically effective amount of compound which will produce an intended physiological effect associated with that agent, and may include such activity as anti-microbial activity including antiviral, antibacterial, antifungal activity, etc. antimicrobial activity such as antiviral activity, antifungal activity, antibacterial activity, especially including or other pharmacological activity, including the treatment of diabetes, and immune suppression, etc. In the case of TLR 7/9 antagonists or the salicylates, which are used in compositions according to the present invention to eliminate, inhibit or reduce the likelihood of inflammation or secondary/side effects, including rejection (foreign body reaction) associated with the use of biomaterials and medical implants, hepatotoxicity associated with the administration of a bioactive agent as otherwise described herein or to treat, inhibit or reduce the likelihood of liver injury secondary to hepatitis, sterile inflammation of the liver, cirrhosis, pancreatitis, etc. as otherwise describe herein, an effective amount of TLR7/9 antagonist and/or salicylate is that amount which significantly decreases hepatotoxicity associated with the administration of the bioactive agent or inflammation of the liver and/or liver injury. In the case of the treatment of hepatitis, non-alcoholic fatty liver disease (NAFLD), including non-alcoholic steatohepatitis (NASH), as a primary condition or secondary to post-liver transplantation or cirrhosis of the liver, etc., an effective amount of a TLR 7/9 antagonist or salicylate and/or bioactive agent is that amount which is effective to treat the condition which is being treated by administering the agent by reducing liver injury associated with the disease state or condition treated. TLR7/9 antagonists and/or salicylate compounds according to the present invention are also useful in effective amounts for treating and/or reducing the likelihood of inflammation of the pancreas (pancreatitis).

In preferred aspects of the invention, the amount of TLR 7/9 antagonist or salicylate which is administered in an effective amount to a patient or subject e.g., to reduce, inhibit or reduce the likelihood (prevent) inflammation associated with implants from surgery, etc., hepatotoxicity of the coadministered bioactive agent, to inhibit or down regulate sterile inflammation or liver injury or to treat hepatitis (i.e., reduce liver injury associated with hepatitis), NAFLD, NASH and/or cirrhosis, etc. or to treat and/or inhibit or reduce the likelihood of pancreatitis as otherwise described herein, is an effective amount preferably falling within the range from about 0.005-0.0.01 mg/kg to about 25 mg/kg, about 0.1 mg/kg to about 20 mg/kg, about 0.5 mg/kg to about 15 mg/kg, about 1.0 mg/kg to about 12.5 mg/kg, about 1.5 mg/kg to about 10 mg/kg, about 2.5 mg/kg to about 7.5 mg/kg, about 3.0 mg/kg to about 5 mg/kg, about 4 mg/kg to about 4.5 mg/kg, about 4 mg/kg to about 6 mg/kg. It is noted that in the case of the use of salicylate, especially aspirin, the amount or concentration of compound which may be used to inhibit or reduce the likelihood of inflammation and side effects from implants, inhibit and/or reduce liver injury, including liver injury associated with the treatment of hepatitis, including viral hepatitis (hepatitis A, B, C, D or E), as well as other indications or conditions as described herein, is substantially less than the amount of salicylate which is required to inhibit hepatitis virus (especially hepatitis C virus) per se. This distinguishes low doses of salicylate of the present invention (low dose effective amounts) from salicylate methods which are required for cox-2 and NFκB inhibition (e.g., hepatitis C virus inhibition, among others), which is considerably higher and increases the risk of increased hepatotoxicity and liver injury. One of ordinary skill in the art may readily adjust the amount of TLR 7/9 antagonist or salicylate to influence and/or reduce inflammation or side effects associated with implants or the hepatotoxicity/liver injury of the coadministered bioactive agent. These amounts are also effective to inhibit sterile inflammation or liver injury as otherwise described herein or treat one or more disease states or conditions (hepatitis, NAFLD, NASH, cirrhosis, pancreatitis, etc.) as otherwise disclosed herein by reducing liver injury associated with those disease states and/or conditions well within the teachings of the present invention. In the case of preserving a liver after removal from a transplant donor and prior to transplantation in a patient, the concentration of TLR 7/9 or salicylate compound used to preserve the liver preferably falls within the same concentrations which are otherwise disclosed hereinabove, with reference to the weight of the liver to be preserved. Note that the active compound TLR 7/9 antagonist or salicylate preferably is formulated in solution to preserve a liver to be transplanted.

The bioactive agent which is administered is that amount effective to produce an intended therapeutic result and may vary widely. The amount of bioactive agent used in the instant invention to be combined with the TLR 7/9 antagonist and/or salicylate compound and carrier materials to produce a single dosage form will vary depending upon the host treated, the particular mode of administration, the level of hepatotoxicity produced, etc. Preferably, the compositions should be formulated so that a therapeutically effective dosage of between about 0.1 μg/kg and 25 mg/kg, about 0.50 μg/kg and 20 mg/kg, about 1 μg/kg and 20 mg/kg about 5 μg/kg to about 15 mg/kg, about 500 μg/kg to about 10 mg/kg patient/day of the compound can be administered to a patient receiving these compositions.

In preferred aspects of the invention, the use of an effective amount of a TLR 7/9 antagonist or salicylate as otherwise described herein, reduces the hepatotoxicity of a bioactive agent which produces hepatotoxicity in the absence of TLR7/9 and/or salicylate of at least about 5-10%, at least about 20%, at least about 30%, at least about 40%, at least about 50%, at least about 60%, at least about 70%, at least about 80%, at least about 90%, at least about 95%, at least about 97%, at least about 99%, at least about 99.5% and at least about 100% (i.e., no appreciable hepatotoxicity can be detected in the patient or subject).

The term "biomaterial" is used to describe a material which may be natural or man-made, that comprises whole or part of a biomedical device which performs, augments, or replaces a natural function in a patient or subject. For purposes of the present invention, a biomaterial is a nonviable material used in a biological system which often produces inflammation when introduced into a patient or subject. A biomaterial is a material that is used and adapted for a medical or dental application. Biomaterials may have numerous functions, such as being used for insulin pumps, heart-vales or related medical structures or alternatively these materials may have a more interactive functionality. Biomaterials are used in medical and dental applications including medical devices, dental implants, surgery, and drug delivery. Biomaterials are generally constructed of polymeric materials including plastics, metals and/or ceramics among other materials and include such materials as steel, titanium, silicone, polyester and polypropylene, among others. Biomaterials may include naturally occurring exogenous cellular and tissue material which is incorporated into a patient or subject for some therapeutic advantage.

The term "implant" is used to describe a medical or biomaterials device manufactured to replace a missing biological structure, support a damaged biological structure, or enhance an existing biological structure. Medical implants are man-made devices, in contrast to a transplant, which is a transplanted biomedical tissue. The surface of implants that contact the body might be made of a biomedical material such as titanium, silicone or apatite depending on what is the most functional. In some cases implants contain electronics e.g. artificial pacemaker, insulin monitors and cochlear implants. Some implants are bioactive, such as subcutaneous drug delivery devices in the form of implantable pills or drug-eluting stents. Exemplary implants include surgical clips and sutures, surgical mesh, breast implants, glucose sensors, artificial heart-valves and pacemakers among numerous other devices.

Among the most common types of medical implants are the pins, rods, screws and plates used to anchor fractured bones while they heal. Electrically-powered implants include artificial pacemakers which help to regulate heart rhythms are another example of a medical implant. Bio-implants include biomaterial which is implanted into a person's body to replace damaged tissue. Common areas of application include orthopedic (especially maxillofacial) re-constructive prosthesis, cardiac prostheses (artificial heart valves like the Chitra heart valve), skin and cornea.

Other implants are contemplated in the present invention as well. Dental implants are one of the few medical devices which permanently cross the boundary between the inside and the outside of the body, since the base of the implant is osseointegrated in the bone of the mandible or maxilla and the top of the implant is in the mouth, where it can be crowned with an artificial tooth. Orthopedic implants often refer to devices that are placed over or within bones to hold a fracture reduction while prosthesis refers to devices that replace a part or whole of a defunct joint. In this context implants may be placed within or outside the body.

There are many types of orthopedic implants and each orthopedic implant is designed to correct the affected joint so that it withstand the movement and stress associated and to enhance mobility and decrease pain. Broadly speaking, orthopedic implants are available for the hip, knee, shoulder and elbow. And include the following, among others:

Safety Locking Plates
Interlocking Nail
Nails, Wires & Pins
Cranio Maxillofacial Implants
Mini Fragment Implants
Small Fragment Implants
Large Fragment Implants
Cannulated Screws
DHS/DCS & Angled Blade Plates
Hip Prosthesis
ACL/PCL Reconstruction System
Spine Surgery
External Fixators The term TLR 7/9 antagonist is used to describe compounds which antagonize the toll-like receptors 7 and/or 9. TLR 7/9 are proteins which are members of the toll-like receptor (TLR) family which plays a fundamental role in pathogen recognition and activation of innate immunity. TLRs are highly conserved from Drosophila to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression.

TLR 7 is predominantly expressed in lung, placenta, and spleen Imiquimod acts upon TLR 7. TLR7 recognises single stranded RNA in endosomes, which is a common feature of viral genomes which are internalised by macrophages. TLR 9, like TLR 7, is also a toll-like receptor. It recognizes unmethylated CpG sequences in DNA molecules. CpG sites are relatively rare (~1%) on vertebrate genomes in comparison to bacterial genomes or viral DNA. TLR9 is expressed by numerous cells of the immune system such as dendritic cells, B lymphocytes and natural killer (NK) cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I inteferon and IL-12.

Inhibitors of TLR 7 and/or TLR 9 for use in the present invention include, for example, chloroquine, hydroxychloroquine, quinacrine, 2'O-methyl-modified RNAs from Provita Biotherapeutics, IRS 954, IRS 869 and IRS 661 from Dynavax, ODN2088 from Invivogen, Su50 from Idera Pharmac, CPG 52364, IMO-3100 and the oligonucleotides which are presented in FIG. 8 hereof, as well as the following oligonucleotides:

```
TLR 9 Antagonists
5'-CTATCTGACGTTCTCTGT-3'        SEQ. ID NO: 19

5'-CTATCTGUCGTTCTCTGT-3'        SEQ. ID. NO: 20

5'-CTATCTGACRTTCTCTGT-3'        SEQ. ID. NO: 21

5'-CTATCTGUCRTTCTCTGT-3'        SEQ. ID. NO: 22

5'-TCCTGGAGGGGAAGT-5'           SEQ. ID. NO: 23

5'-TCCTGGCGGGGAAGT-3'           SEQ. ID. NO: 24

TLR7 Antagonist
5'-UGCUGUUCUG-X-GUCUUGUCGU-3'   SEQ. ID. NO: 25
```

Wherein each of the above oligonucleotides contain phosphorothioate backbones. The first six sequences (SEQ ID NO: 19-24) are oligodeoxynucleotides and the seventh sequence (SEQ ID NO: 25) is an oligoribonucleotide and wherein R is a 2'-deoxy-7-deazaguanosine, X is a glycerol linker (see below), G/A/U indicate 2'-O-methyl-ribonucleotide modifications within the oligonucleotide and each G (in sequence 25) represents 7-deazaguanosine as described below.

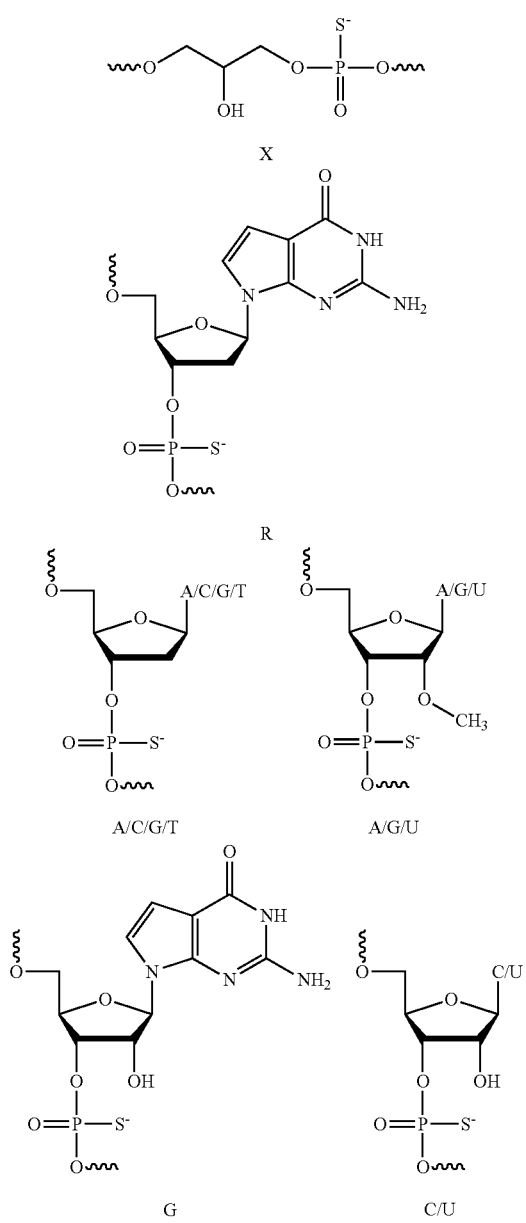

See, *J. Med. Chem.*, 2009, 5, 551-558 and *J. Med. Chem.*, 2009, 52, 5108-5114, (each of which is incorporated by reference in its entirety herein), Other TLR 7 and/or 9 antagonists are found in FIG. 8 hereof and comprise 2'-O-methyl modified oligonucleotides, which oligodeoxynucleotides containing phosphorothioate backbones are modified using 2'-O-methyl uracil and 2'-O-methylguanosine. The effect is non-sequence specific, although oligonucleotides containing from 7 to 50 mer, about 10 to 35 mer, more preferably about 20 to 25 mer, about 21 mer (FIG. 8) wherein the oligonucleotide contains at least two 2'-O-methylated nucleosides selected from the group consisting of 2'-O-methyluracil and 2'-O-methylguanosine nucleoside. In alternative embodiments the oligonucleotides (oligodeoxynucleotides) contain at least one stretch of 3-5 guanine nucleotides in a row and comprise from about 7 to about 50 mer, about 10 to 35 mer, about 12 to 30 mer, about 15 to 28 mer, about 15 to about 25 mer, about 20 to about 25 mer, about 18 to about 20 mer. An exemplary group of oligonucleotides having these features is set forth in FIG. 9, attached hereto.

Additional nucleotides which inhibit TLR 7 and/or 9 include phosphorothioate DNA oligodeoxynucleotides (containing a phosphorothioate backbone) comprising at least one CpG dinucleotide group wherein said dinucleotide group comprises at least one (preferably one) 2'-O-methylcytidine and/or a 2'-O-methylguanosine unit, a 5-methylcytidine or a 2'-O-methyl-5-methyl cytidine unit or a methylphosphonate linkage between the C and G nucleotide units, wherein said oligonucleotide ranges from 7 to about 50 mer, about 10 to about 35 mer, about 15 to about 25 mer, about 20 to about 25 mer, about 18 to 20 mer.

The term "foreign body reaction" is used to describe inflammation and the related secondary effects (side effects) which occur as a consequence of a body's response to the unnatural introduction or implantation of biomaterials in an implant. In addition to inflammation, foreign body reaction results in a series of biochemical and cellular responses (secondary or side effects) including deposition of cells and collagenous matrix around the device and/or biomaterial; pain and swelling at the site of the biomaterial; limiting the function/reducing the residence time of the biomaterial and/or medical device; causing infections due to bacterial biofilm formation. Until the advent of the present invention, there were no therapeutic strategies which could be employed to limit the foreign body reaction other than the administration of steroids, which cause significant untoward side effects.

The term "hepatitis" is used to describe a liver condition which implies injury to the liver characterized by the presence of inflammatory cells in the tissue of the organ. The condition can be self-limiting, healing on its own, or can progress to scarring of the liver. Hepatitis is acute when it lasts less than six months and chronic when it persists longer than six months. A group of viruses known as the hepatitis viruses cause most cases of liver damage worldwide. Hepatitis can also be due to toxins (notably alcohol), other infections or from autoimmune process. Hepatitis may run a subclinical course when the affected person may not feel ill. The patient becomes unwell and symptomatic when the disease impairs liver functions that include, among other things, removal of harmful substances, regulation of blood composition, and production of bile to help digestion.

Hepatitis includes hepatitis from viral infections, including Hepatitis A through E (A,B,C, D and E—more than 95% of viral cause), Herpes simplex, Cytomegalovirus, Epstein-Barr virus, yellow fever virus, adenoviruses; non-viral infections, including toxoplasma, Leptospira, Q fever, rocky mountain spotted fever, alcohol, toxins, including amanita toxin in mushrooms, carbon tetrachloride, asafetida, among others, drugs, including paracetamol, amoxycillin, antituberculosis medicines, minocycline and numerous others as described herein; ischemic hepatitis (circulatory insufficiency); pregnancy; autoimmune conditions, including Systemic Lupus Erythematosus (SLE); metabolic diseases, e.g. Wilson's disease, hemochromatosis and alpha one antitrypsin deficiency; and non-alcoholic steatohepatitis.

The term "sterile inflammation" is used to describe inflammation of the liver which is triggered by intracellular molecules released from dying cells that have lost integrity of their plasma membrane. This inflammation occurs in the absence of causative agents such as viruses or bacteria and alcohol. A number of intracellular molecules have been identified that can stimulate other cells to produce proinflammatory cytokines and chemokines. Such proinflammatory cellular molecules are thought to function by engaging receptors on cytokine-producing cells. If left untreated, sterile inflammation may progress to non-alcoholic fatty liver disease (NAFLD), non-alcoholic steatohepatitis (NASH) or cyrrhosis.

The term "non-alcoholic steatohepatitis" or "NASH" is used to describe a condition of the liver in which inflammation is caused by a buildup of fat in the liver. NASH is part of a group of liver diseases, known as nonalcoholic fatty liver disease, in which fat builds up in the liver and sometimes causes liver damage that gets worse over time (progressive liver damage). "Non-alcoholic fatty liver disease" (NAFLD) is fatty inflammation of the liver which is not due to excessive alcohol use. It is related to insulin resistance and the metabolic syndrome, and may respond to treatments originally developed for other insulin resistant states (e.g. diabetes mellitus type 2), such as weight loss, metformin and thiazolidinediones. Non-alcoholic steatohepatitis (NASH) is the most extreme form of NAFLD, which is regarded as a major cause of cirrhosis of the liver of unknown cause.

Although the cause is not known, NASH seems to be related to certain other conditions, including obesity, high cholesterol and triglycerides, and diabetes. Historically, treatment for NASH involved controlling those underlying diseases. Type II diabetes treating agents administered in combination with a salicylate as otherwise described herein may be used in combination to inhibit sterile inflammation or to treat and/or reduce the likelihood of NASH, NAFLD and/or cirrhosis.

The exact cause of NASH is not known. It most commonly affects people who are middle-aged and are overweight or obese, have high cholesterol and triglycerides, or have diabetes. Despite these indications, NASH can occur in people who have none of these risk factors. Excess body fat along with high cholesterol and high blood pressure are also signs of a condition called metabolic syndrome. This condition is closely linked to insulin resistance.

Along with excess fat in the liver, which many people have, several other factors may contribute to the liver damage and place individuals at risk. These are:

Resistance to insulin, which means that the body can't use sugar (glucose) in the way it should. Normally, your body makes insulin after you eat a meal that has sugar in it. Insulin helps the extra sugar in your blood get into your muscles and liver. If your body does not respond to insulin in this way, then the sugar level in your blood will stay high. This is how insulin resistance can increase your chance of developing type 2 diabetes.

Changes in how the liver makes fat and what the liver does with fat that is delivered to it by the intestines. Other factors that have been known to contribute to NASH include:

Having had surgeries that shorten the intestines, the stomach, or both, such as jejunal bypass operation or biliopancreatic diversion.

Using a feeding tube or other method of receiving nutrition for a long time.

Using certain medicines, including amiodarone, glucocorticoids, synthetic estrogens, and tamoxifen.

NASH is a condition that may get worse over time (called a progressive condition). For this reason, a patient may have no symptoms until the disease progresses to the point that it begins to affect the way the liver works (liver function). As liver damage gets worse, symptoms such as tiredness, weight loss, and weakness may develop. It may take many years for NASH to become severe enough to cause symptoms. In some cases, the progress of the condition can stop and even reverse on its own without treatment. But in other cases NASH can slowly get worse and cause scarring (fibrosis) of the liver, which leads to cirrhosis. Cirrhosis means that liver cells have been replaced by scar tissue. As more of the liver becomes scar tissue, the liver hardens and can't work normally.

The term "cirrhosis of the liver" or "cirrhosis" is used to describe a chronic liver disease characterized by replacement of liver tissue by fibrous scar tissue as well as regenerative nodules (lumps that occur as a result of a process in which damaged tissue is regenerated), leading to progressive loss of liver function. Cirrhosis is most commonly caused by fatty liver disease, including NASH, as well as alcoholism and hepatitis B and C, but has many other possible causes. Some cases are idiopathic, i.e., of unknown cause. Ascites (fluid retention in the abdominal cavity) is the most common complication of cirrhosis and is associated with a poor quality of life, increased risk of infection, and a poor long-term outcome. Other potentially life-threatening complications are hepatic encephalopathy (confusion and coma) and bleeding from esophageal varices. Cirrhosis has historically been thought to be generally irreversible once it occurs, and historical treatment focused on preventing progression and complications. In advanced stages of cirrhosis, the only option is a liver transplant. The present invention may be used to limit, inhibit reduct the likelihood or treat cirrhosis of the liver without regard to its etiology.

The term "physical trauma" or "acute physical trauma" refers to physical trauma (serious injury) which occurs to a patient over a short duration of time (e.g., the result of an accident or physical insult) resulting in an acute injury, in this case, to the liver. "Chemical trauma" or "acute chemical trauma" refers to serious injury which occurs to a patient over a short duration as a consequence of chemical toxicity, including drug-induced toxicity or trauma. Drug-induced acute liver trauma, including acetaminophen-induced acute liver trauma, is acute liver injury which occurs as a result or consequence of exposure to a drug (e.g., drug overdose), especially acetaminophen toxicity. Compounds according to the present invention are useful for reducing the injury to the liver which occurs from physical and chemical trauma, especially including drug-induced (drug overdose) and acetaminophen-induced acute liver trauma.

The term "hepatotoxicity" or "drug induced hepatotoxicity" is used to describe hepatotoxicity (liver toxicity) which occurs as a consequence of chemical-driven liver damage. The liver plays a central role in transforming and clearing chemicals and is susceptible to the toxicity from these agents. Certain medicinal agents when taken in overdoses and sometimes even when introduced within therapeutic ranges may injure the organ. Other chemical agents such as those used in laboratories and industries, natural chemicals (e.g. microcystins) and herbal remedies can also induce hepatotoxicity. Chemicals that cause liver injury are called hepatotoxins. More than 900 drugs have been implicated in causing liver injury and it is the most common reason for a drug to be withdrawn from the market. Chemicals often cause subclinical injury to liver which manifests only as abnormal liver enzyme tests. Drug induced liver injury is responsible for 5% of all hospital admissions and 50% of all acute liver failures.

Drugs and other chemicals may produce a wide variety of clinical and pathological hepatic injury. Biochemical markers (i.e. alanine transferase, alkaline phosphatase and bilirubin) are often used to indicate liver damage. Liver injury is defined as an increase in either (a) ALT level more than three times of upper limit of normal (ULN), (b) ALP level more than twice ULN, or (c) total bilirubin level more than twice ULN when associated with increased ALT or ALP. Liver damage is further characterized into hepatocellular (predominantly initial alanine transferase elevation) and cholestatic (initial alkaline phosphatase rise) types. However these are not mutually exclusive and mixed type of injuries are often encountered.

In the present invention, the inclusion of a salicylate compound as otherwise described herein produces a substantial reduction (at least about 10% reduction, at least about 20% reduction, at least about 25% reduction, at least about 30% reduction, at least about 35% reduction, at least about 40% reduction, at least about 45% reduction, at least about 50% reduction, at least about 60% reduction, at least about 65% reduction, at least about 75% reduction, at least about 85% reduction, at least about 90% reduction or more) of hepatotoxicity such that at least one of alanine transferase (ALT) activity, alkaline phosphatase (ALP) activity and total bilirubin level, preferably at least ALT and ALP and preferably ALT, ALP and bilirubin levels are all reduced by levels as described above.

Specific histo-pathological patterns of liver injury from drug induced damage are discussed below.

Zonal Necrosis

This is the most common type of drug induced liver cell necrosis where the injury is largely confined to a particular zone of the liver lobule. It may manifest as very high level of ALT and severe disturbance of liver function leading to acute liver failure.

Causes:

Acetaminophen (Tylenol), Carbon Tetrachloride

Hepatitis

In this pattern hepatocellular necrosis is associated with infiltration of inflammatory cells. There can be three types of drug induced hepatitis. (A) viral hepatitis type picture is the commonest, where histological features are similar to acute viral hepatitis. (B) in the focal or non specific hepatitis scattered foci of cell necrosis may accompany lymphocytic infiltrate. (C) chronic hepatitis type is very similar to autoimmune hepatitis clinically, serologically as well as histologically.

Causes:

(a) Viral hepatitis like: Halothane, Isoniazid, Phenytoin (b) Focal hepatitis: paraaminobenzoic acid, oral contraceptives, aspirin (c) Chronic hepatitis: Methyldopa, Diclofenac Cholestasis Liver injury leads to impairment of bile flow and clinical picture is predominated by itching and jaundice. Histology may show inflammation (cholestatic hepatitis) or it can be bland without any parenchymal inflammation. In rare occasions it can produce features similar to primary biliary cirrhosis due to progressive destruction of small bile ducts (Vanishing duct syndrome).

Causes:

(a) Bland: Oral contraceptive pills, anabolic steroid, Androgens (b) Inflammatory: Allopurinol, Co-amoxiclav, Carbamazepine (c) Ductal: Chlorpromazine, flucloxacillin Steatosis Hepatotoxicity may manifest as triglyceride accumulation which leads to either small droplet (microvesicular) or large droplet (macrovesicular) fatty liver. There is a separate type of steatosis where phospholipid accumulation leads to a pattern similar to the diseases with inherited phospholipid metabolism defects (e.g. Tay-Sachs disease)

Causes:

(a) Microvesicular: Ketoprofen, Tetracycline (b) Macrovesicular: Acetaminophen, methotrexate (c) Phospholipidosis: Amiodarone, Total parenteral nutrition Granuloma Drug induced hepatic granulomas are usually associated with granulomas in other tissues and patients typically have features of systemic vasculitis and hypersensitivity. More than 50 drugs have been implicated.

Causes:

Allopurinol, Phenytoin, Isoniazid, Quinine, Penicillin, Quinidine

Vascular Lesions

Vascular lesions result from injury to the vascular endothelium.

Causes:

Venoocclusive disease: Chemotherapeutic agents, bush tea

Peliosis hepatis: anabolic steroid

Hepatic vein thrombosis: Oral contraceptives

The term "pharmaceutically acceptable salt" is used throughout the specification to describe a salt form of one or more of the compounds described herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids, especially salts of carboxylic acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids in compositions according to the present invention. The term "salt" shall mean any salt consistent with the use of the compounds according to the present invention. As used herein, the term "salt" shall mean a pharmaceutically acceptable salt, consistent with the use of the compounds as pharmaceutical agents.

The term "therapeutic index" (also known as therapeutic ratio), is a comparison of the amount of a therapeutic agent that causes the therapeutic effect to the amount that causes toxic effects, as used in the present invention, hepatotoxicity. Quantitatively, it is the ratio given by the dose causing hepatotoxicity divided by the therapeutic dose. A measure of therapeutic index used herein is the hepatotoxic dose of a drug for 50% of the population ($TD_{50}$) divided by the minimum effective dose for 50% of the population ($ED_{50}$). A high therapeutic index is preferable to a low one: this corresponds to a situation in which one would have to take a much higher amount of a drug to do harm than the amount taken to provide a therapeutic effect.

In the past, a drug with a narrow therapeutic range (i.e. with little difference between hepatotoxic and therapeutic doses) may have its dosage adjusted according to measurements of the actual blood levels achieved in the person taking it. This may be achieved through therapeutic drug monitoring (TDM) protocols. However, using the present invention (an effective amount of one or more of a salicylate and/or a TLR7/9 antagonist, especially aspirin, as otherwise described herein), the therapeutic index of a bioactive agent administered in the absence of a salicylate and/or a TLR7/9 antagonist, especially aspirin, as otherwise described herein, may be increased appreciably, i.e., at least about 10%, at least about 15%, at least about 20%, at least about 25%, at least about 30%, at least about 35%, at least 40%, at least 45%, at least 50%, at least 60%, at least 75%, at least 90%, at least 95%, at least about 100%, at least about 150% (at least 1.5 times the therapeutic index without coadministration of a salicylate as described herein), at least about 200%, at least about 300%, at least about 500%, at least about 1000% (at least 10 times the original therapeutic index).

The term "coadministration" or "combination therapy" is used to describe a therapy in which a salicylate and/or a TLR 7/9 antagonist which reduces or ameliorates hepatotoxicity of another agent is combined with a bioactive agent as otherwise described herein. The bioactive agent used in the present invention may be used to treat a wide range of disease states and/or conditions and may exhibit a wide variety of pharmacological or physiological effects. Although the term coadministration preferably includes the administration of two compounds, at least one salicylate or TLR 7/9 antagonist as otherwise described herein as well as a bioactive to the patient at the same time, it is not necessary that the compounds be administered to the patient at the same time, although effective amounts of the individual compounds generally will be present in the patient at the same time. Compounds according to the present invention are preferably coadministered in a single composition, preferably which is at least sustained or controlled release with respect to the hepatotoxicity reducing salicylate compound which is used. In other instances, both the hepatotoxicity reducing salicylate compound and the bioactive agent are both formulated for sustained or controlled release administration.

The term "sustained release" or "controlled release" is used to describe administration of a salicylate and/or TLR7/9 antagonist and/or a bioactive agent as otherwise described herein over a sustained or controlled period of time, oftentimes for periods of at least about 4 hours, at least about 6 hours, at least about 8 hours, at least about 10 hours, at least about 12 hours, at least about 16 hours, at least about 20 hours, at least about 24 hours, at least about 2 days up to a week or more. In certain embodiments which are delivered from transdermal patches, release may occur over several weeks or more. The release rate for the salicylate according to the present invention may differ from the release rate of the TLR 7/9 antagonist or the bioactive agent. Sustained or controlled release compositions according to the present invention contrast with delayed release, immediate release or "bolus" release administration of compounds or delayed release compounds, which represent alternative embodiments of the present invention. Immediate release compositions are those which release agents substantially immediately as a bolus dose. Delayed release compositions are those which release agents in a somewhat slower manner than an immediate release composition, but which do not release agents in a controlled or sustained release manner. See, for example, fda.gov/cder/guidance/4964dft.htm at fda.gov/cder, among other sources.

In order to provide sustained or controlled release compositions hereunder, well known techniques for influencing the release rate of compositions may be used. Conventional formulation techniques may be used in order to provide sustained or controlled release compositions according to the present invention. Sustained or controlled release compositions according to the present invention may be provided wherein salicylate and bioactive agent are delivered from the same sustained or controlled release matrix in a tablet, capsule, transdermal patch, topical creams or the like, or alternatively, each of the salicylate compound and the bioactive agent, although being delivered from the same capsule, tablet, patch, cream, etc., may be delivered from different matrices which release compound therefrom at differing rates in order to provide effective concentrations in the blood, plasma and/or serum of the patient.

Sustained or controlled release formulations which may be used to formulate the present compositions include those which are disclosed in inter alia, U.S. Pat. Nos. 4,508,702; 4,520,009; 4,970,081; 4,988,679; 4,753,801; 4,755,387; 4,629,621; 4,308,251; 4,302,440; 5,004,613; 4,460,368; 4,555,399; 4,316,884; 4,025,613; 4,829,523; and 4,867,984, relevant portions of which patents are incorporated by reference herein.

Pursuant to the present invention, the inclusion of a salicylate compound and/or a TLR7/9 antagonist as otherwise described herein produces a substantial reduction (at least about 5-10% reduction, at least about 20% reduction, at least about 25% reduction, at least about 30% reduction, at least about 35% reduction, at least about 40% reduction, at least about 45% reduction, at least about 50% reduction, at least about 60% reduction, at least about 65% reduction, at least about 75% reduction, at least about 85% reduction, at least about 90% reduction) of hepatotoxicity caused by a bioactive agent as otherwise described herein such that at least one of alanine transferase (ALT) activity, alkaline phosphatase (ALP) activity and total bilirubin level, preferably at least ALT and ALP and preferably ALT, ALP and bilirubin levels are all reduced by levels as described above.

Compounds according to the present invention may be used in pharmaceutical compositions having biological/pharmacological activity for the treatment of, for example, microbial infections, including viral infections such as HIV infections and hepatitis infections, including hepatitis A, B, C, D and E, *Mycobacterial* infections, especially *Mycobacterium tuberculosis* (tuberculosis) infections, fungal infections, including Candida infections, among numerous others, for the treatment of diabetes and for the treatment of skin conditions such as acne, as well as numerous other disease states and/or conditions as otherwise described herein. Virtually any bioactive agent which produces hepatotoxicity may be utilized in the present invention in combination with an effective amount of a salicylate compound and/or TLR 7/9 antagonist as otherwise described herein in order to reduce the hepatotoxicity associated with the administration of the bioactive agent.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, by inhalation spray, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously. Preferred routes of administration include oral administration, sublingual or buccal administration and pulmonary administration (by inhaler/inhalation spray).

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions, preferably as sustained release compositions, at least for the salicylate administered. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application. Suitable topical formulations are readily prepared for each of these areas or organs.

Topical application also can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In preferred aspects of the invention, the amount of salicylate and/or TLR 7/9 antagonist which is administered to a patient or subject to reduce the hepatotoxicity of the coadministered bioactive agent is an effective amount falling within the range from about 0.01 mg/kg to about 25 mg/kg, about 0.1 mg/kg to about 20 mg/kg, about 0.5 mg/kg to about 15 mg/kg, about 1.0 mg/kg to about 12.5 mg/kg, about 1.5 mg/kg to about 10 mg/kg, about 2.5 mg/kg to about 7.5 mg/kg, about 3.0 mg/kg to about 5 mg/kg, about 4 mg/kg to about 4.5 mg/kg. One of ordinary skill in the art may adjust the amount of salicylate and/or TLR 7/9 antagonist coadministered with a bioactive agent to influence and reduce the hepatotoxicity of the coadministered bioactive agent. The amount of salicylate used in the instant invention to be combined with a bioactive agent and carrier materials to produce a single dosage form will vary depending upon the host treated, the particular mode of administration, the therapeutic target, the level of hepatotoxicity produced by a bioactive agent, etc.

The amount of bioactive agent used in the instant invention to be combined with the salicylate compound and/or TLR 7/9 antagonist and carrier materials to produce a single dosage form will vary depending upon the host treated, the particular mode of administration, etc. Preferably, the compositions should be formulated so that a therapeutically effective dosage of between about 0.1 µg/kg and 25 mg/kg, about 0.50 µg/kg and 20 mg/kg, about 1 µg/kg and 20 mg/kg about 5 µg/kg to about 15 mg/kg, about 500 µg/kg to about 10 mg/kg patient/day of the compound can be administered to a patient receiving these compositions.

Preferably, pharmaceutical compositions in dosage form according to the present invention comprise a therapeutically effective amount of at least about 5 µg of bioactive agent, at least about 25 µg of bioactive agent, at least about 100 µg of bioactive agent, at least about 500 µg of bioactive agent, at least about 1 mg of bioactive agent, at least about 10 mg of bioactive agent, at least about 15 mg of bioactive agent, at least about 25 mg of bioactive agent, at least 50 mg of bioactive agent, at least 60 mg of bioactive agent, at least about 75 mg of bioactive agent, at least about 100 mg of bioactive agent, at least 150 mg of bioactive agent, at least 200 mg of bioactive agent, about 250 mg of bioactive agent, about 300 mg of bioactive agent, about 350 mg of bioactive agent, about 400 mg of bioactive agent, about 500 mg of bioactive agent, about 750 mg of bioactive agent, about 1 g (1000 mg) of bioactive agent, alone or in combination with a therapeutically effective amount of at least one additional bioactive agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated. The amount of salicylate compound which is included in a pharmaceutical composition or otherwise administered to a patient or subject will vary with the ability of the bioactive agent to induce heptatoxicity.

Coadministration of the active compounds may range from continuous (intravenous drip) to one or more oral or inhalation (intratracheal) administrations per day (for example, a single sustained or controlled release dose, B.I.D. or Q.I.D.) and may include oral, pulmonary, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance, in addition to the fact that oral dosage forms lend themselves more easily to sustained or controlled release administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the faint of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In preferred aspects, the present invention also relates to pharmaceutical compositions in oral dosage form comprising effective amounts of TLR7/9 antagonists and/or a salicylate (preferably aspirin) in combination with effective amounts of a bioactive agent according to the present invention, optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

The pharmaceutical compositions of the invention are safe and effective for use in the therapeutic methods according to the present invention. Although the dosage of the individual components of the composition of the invention may vary depending on the type of active substance administered and optional additional agents as well as the nature (size, weight, etc.) of the subject to be diagnosed, the composition is administered in an amount effective for allowing the pharmacologically active substance to exhibit its inherent therapeutic effect, with reduced hepatotoxicity associated with the coadministration of the compound as otherwise described herein. For example, the composition is preferably administered in sustained release oral, topical, sublingual or buccal dosage forms, from once a day up to two (BID) or four times a day (QID). The form of the pharmaceutical composition of the invention such as a tablet, capsule, powder, solution, suspension etc. may be suitably selected according to the type of substance to be administered.

Not to be limited by way of mechanism, the present inventors have shown that hepatocyte death results in a sterile inflammatory response which amplifies the initial insult and increases liver injury. A clinically important example is acetaminophen induced liver injury in which there is initial toxic injury, followed by innate immune activation. Using mice deficient in TLR9 and the inflammasome components NALP3, ASC and caspase-1, the inventors have identified a non-redundant role for TLR9 and the NALP3 inflammasome in acetaminophen induced injury. There is an initial toxic injury resulting in hepatocyte death. DNA from the apoptotic hepatocytes subsequently activates TLR9, and provides the signal for pro-IL-1$\beta$ and pro-IL-18 transcription. The NALP3 inflammasome provides the second signal for cleavage and activation of these cytokines by caspase-1. Liver sinusoidal endothelial cells express TLR9, up-regulate pro-IL-1$\beta$ and pro-IL-18 in response to DNA from apoptotic hepatocytes, and demonstrate caspase-1 activation in vivo after acetaminophen injury. TLR 7/9 antagonists and salicylates reduce mortality from acetaminophen hepatotoxicity. The protective effect of aspirin on acetaminophen-induced liver injury is not via inhibition of cox-1 or platelet degranulation, but rather by down regulation of pro-inflammatory cytokines. In summary, we have identified a two signal requirement of TLR9 and inflammsome activation for full acetaminophen hepatotoxicity, and demonstrated novel therapeutic approaches to improve survival using a TLR 7/9 antagonist and/or salicylate compound as otherwise described herein.

As described above, another aspect of the invention relates to methods for the preservation of a liver after removal of the liver from a transplant donor and prior to transplantation in a patient, the method comprising exposing said liver after said removal and prior to transplantation to an effective amount of a TLR 7/9 antagonist and/or salicylate compound as described above, optionally in combination with a pharmaceutically acceptable carrier, additive or excipient. In certain aspects of the liver preservation method, the compound is in solution (preferably at a temperature below room temperature) and in further aspects of the invention, the liver is exposed to the solution and the liver and solution are frozen, including cryopreserved optionally in combination with a cryopreservation agent, using methods which are well known in the art, The following description of experiments conducted are presented to exemplify the present invention. They are by way of example only and are not to be taken the limit the invention in any way.

In the following examples, the inventors demonstrate a role for the cellular machinery involved in sterile inflammation in a range of disease models and biological processes. These include sterile liver injury by acetaminophen (APAP), pancreatitis and the foreign body reaction to biomaterials Important components of this machinery are membrane receptors which can detect cellular perturbation and cellular death. We have identified that TLR7 and TLR9 serve an important role in vivo by detecting cellular death. TLRT and TLR9 serve this role by undergoing activation in response to endogenous cellular materials including nucleic acids. We have data that activation of TLR 7 and 9 results in initiation of a sterile inflammatory response in a wide range of clinically important conditions. These include drug induced liver injury (for example APAP), non-alcoholic steatohepatitis, alcoholic steatohepatitis, and even hepatitis caused by hepatitis C and B viral infections. They also have an important role in a wide range of other types of inflammatory diseases, including pancreatitis and the inflammation caused by biomaterials known as the foreign body reaction.

Materials and Methods

Animals.

C57BL/6 mice were purchased from commercial sources. NALP3 −/−, IL-18 −/− ASC −/−, IPAF −/− and TLR9 −/− mice were backcrossed nine generations onto the C57BL/6 background. Caspase 1 −/− mice were backcrossed 5-6 generations onto the C57BL/6 background. These mice have been described previously (39, 40). IL-1β was neutralized in by using the anti-IL-1β antibody from clone B122 (a gift of R. Schreiber, Washington University) at a dose of 0.2 mg/mouse iv twice a day for a total of 48 hours after giving APAP. Control mice received Armenian hamster isotype control antibody. For survival experiments animals were euthanized when they became moribund using criteria of lack of response to stimuli or lack of righting reflex. Animal protocols were approved by the Yale University animal care and use committee. [include references for IPAF −/− (M. Lara-Tejero et al. JEM 2006) and IL-18 −/−. Need to add TLR9 −/− and TLR3 −/−]

Administration of Aspirin Limits Foreign Body Reaction

Two models of the foreign body reaction were tested. In the first model, injection of 150 micron polystyrene beads into the abdominal cavity of C57BL/6 was followed by analysis of cellular infiltrate 24 hours later. In the second model, implantation of a 6 mm disc of silicone subcutaneously was followed by analysis of the foreign body reaction about one month later. The above two models were performed on mice on normal drinking water or with aspirin (60 mg/ml). FIG. 2 shows that the continuous administration of aspirin limits the foreign body reaction to polystyrene beads in the abdominal cavity at 24 hours. The experiment evidenced that the cellular infiltrate at 24 hours was comprised principally of immune cells (neutrophils and macrophages). Although the foreign body reaction was substantially diminished by the continuous administration of aspirin, the composition of the cellular infiltrate was not significantly altered by the administration of aspirin.

Acetaminophen APAP Induced Liver Inflammation, Liver Injury and Mortality is Less in Mice Lacking TLR7 or 9.

Figure 3:
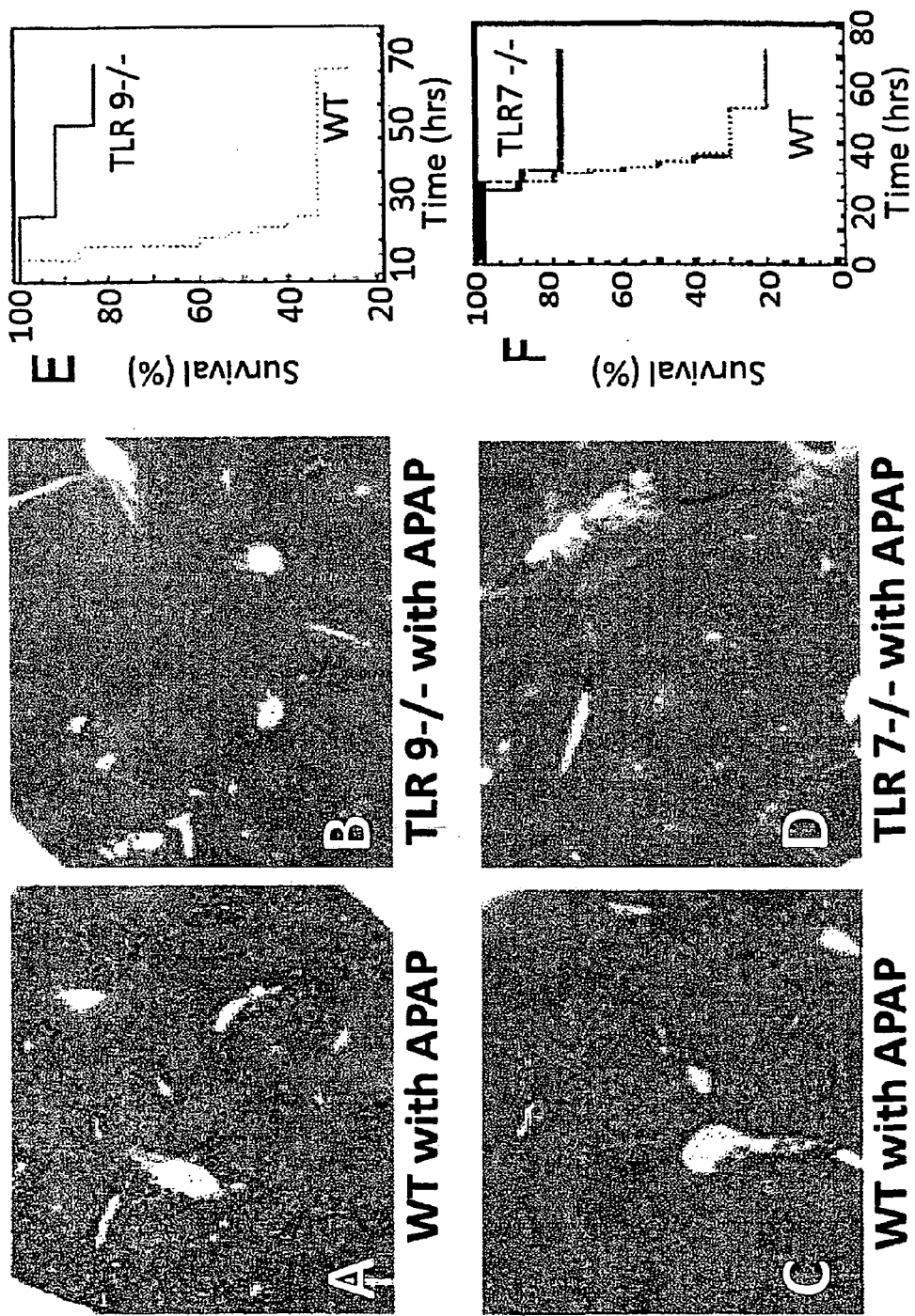
FIG. 3A-F shows that APAP induced liver inflammation, liver injury and mortality is reduced in mice lacking TLR7 and/or 9. A comparison of A and B shows less hemorrhage and cell death in the livers of mice lacking TLR9 compared to wild-type, and a comparison of C and D shows a similar effect of TLR7. Figure E shows less mortality in mice lacking TLR7. The date was generated by a single ip injection of acetaminophen (APAP) at a dose of 500 mg/kg. Data in A to D is taken 12 hours after APAP injection. Date for E and F is over a 3 day period.

APAP (Sigma, Mo.) solution was made fresh for each experiment in PBS at 20 mg/ml and heated in a water bath to 55° C. to dissolve. APAP was dosed at 500 mg/kg and injected I.P after 15 hrs of starvation. Animals were euthanized by ketamine/xylazine injection at 12 hours for collection of serum, isolation of liver lymphocytes or collection of liver tissue for histology, or they were observed every four hours for 72 hours until they reached criteria for euthanasia (lack of response to stimuli or lack of righting reflex). FIGS. 3A and B show less hemorrhage and cell death in the livers of mice lacking TLR9 compared to wild-type and FIGS. 3C and D show a similar affect of TLR7. Figure E shows less mortality in mice lacking TLR9 and Figure F shows less mortality in mice lacking TLR7. The data was generated by a single ip injection of APAP at a dose of 500 mg/kg. Data in Figures A to D was generated 12 hours after APAP and E and F is over a 3 day period.

APAP Induced Liver Inflammation, Liver Injury and Mortality is Less in Mice Treated with a TLR7 or a TLR7/9 Combined Antagonist.

Figure 4:
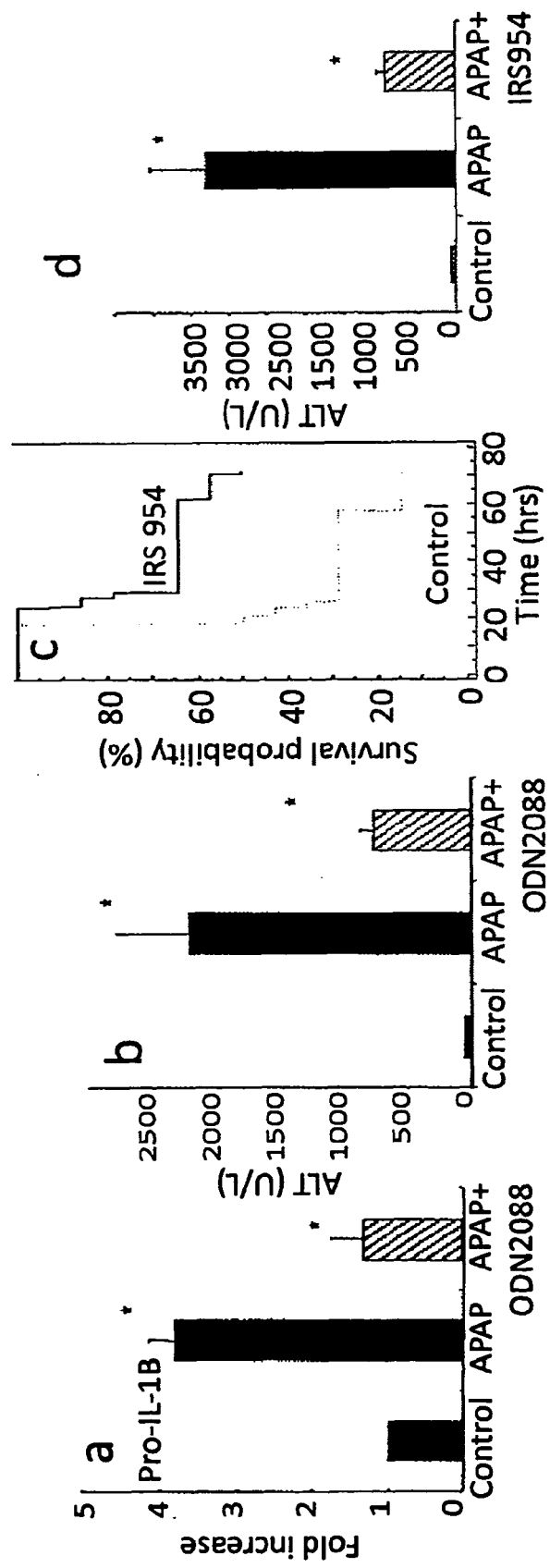
FIGS. 4A-D shows APAP induced liver inflammation, liver injury and mortality is less in wild-type mice treated with a TLR7 or a TLR7/9 combined antagonist.

FIG. 4A shows less up-regulation of inflammatory pro-cytokine mRNA in whole liver tissue of wild-type mice treated with a TLR antagonist. Data was generated 12 hours after injection of APAP. FIG. 4B shows lower increase in serum ALT of wild-typemice treated with a TLR9 antagonist, the data also being generated after 12 hours post injection of APAP. FIG. 4C shows that administration of TLR7 and 9 antagonists resulted in a significantly improved survival in wild-type mice. The data was generated over 72 hours (3 days). FIG. 4D shows lower increases in serum ALT of wild-type mice treated with TLR 7/9 antagonist. Data was generated from 23 hours after injection of APAP.

Figure 5:
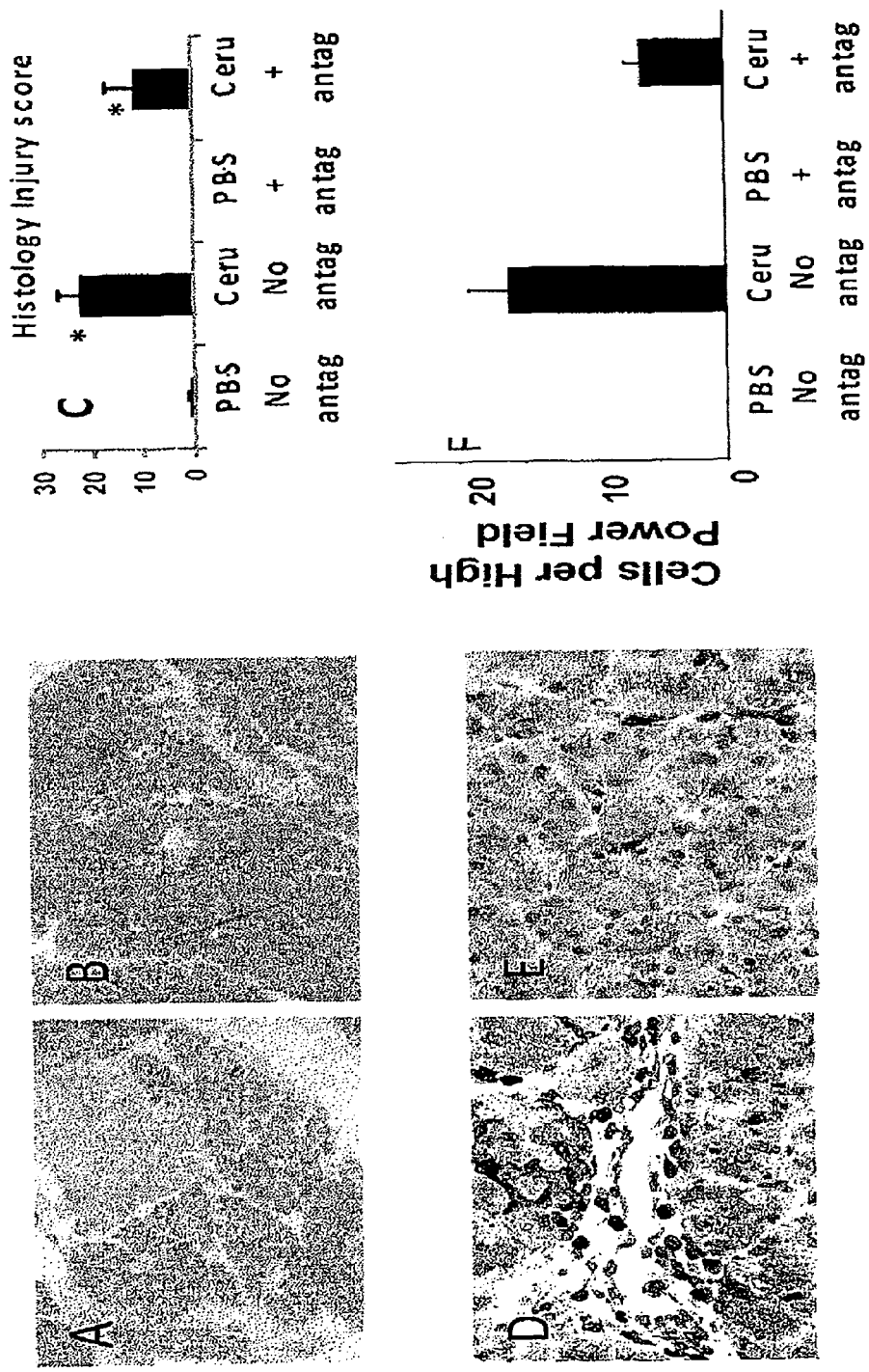
FIGS. 5A-F shows that pancreatic injury and inflammation is less in wild-type mice treated with a TLR 7/9 antagonist. Reduced pancreatic injury in wild-type mice in a cerulin induced model of pancreatitis.

Pancreatitis—Pancreatic Injury and Inflammation is Less in Wild-Type Mice Treated with a TLR7/9 Antagonist Pancreatic injury and inflammation is less in wild-type mice treated with a TLR7/9 antagonist. FIG. 5 shows reduced pancreatic injury in wild-type mice in a cerulin induced model of pancreatitis. 5A shows H & E staining of pancreas from wild-type mouse given cerulin (agent which induces pancreatitis) without TLR7/9 antagonist. FIG. 5B shows wild-type mouse given cerulin without TLR. FIG. 5C shows a summary of histological scoring which grades edema, inflammation and cell death, showing less overall injury when a TLR7/9 antagonist is given along with cerulin. FIGS. 5D and E show that staining for neutrophils evidences that neutrophil infiltrate is less in the pancreas with TLR7/9 antagonist treatment. FIG. 5F shows the quantification of reduced neutrophil infiltrate with TLR7/9 antagonist treatment.

Foreign Body Reaction—Reduced Foreign Body Reaction in the Absence of Pathways Activated by TLR7 and TLR9

Figure 6:
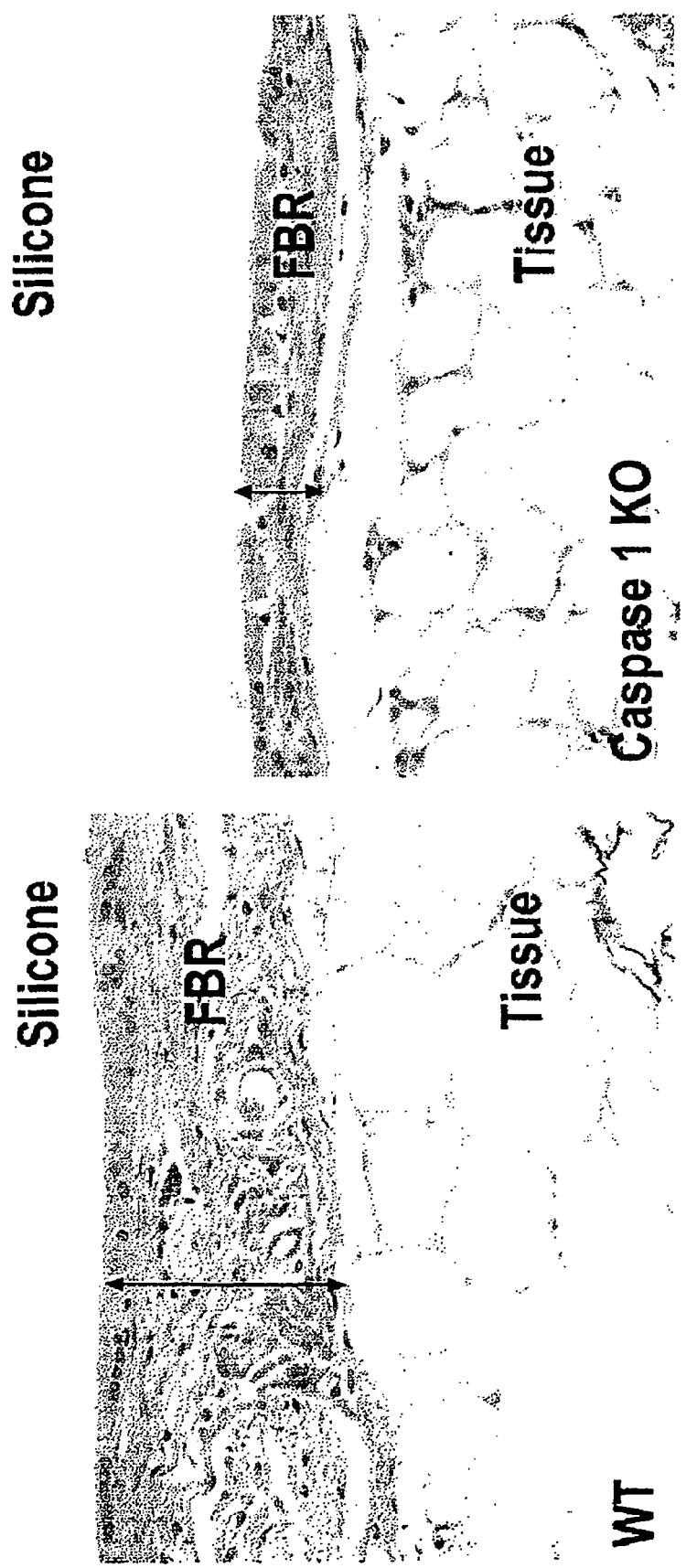
FIG. 6 shows significantly reduced foreign body reaction in the absence of pathways activated by TLR 7 and 9. After the implantation of 6 mm silicone disc the foreign body reaction was quantified by examining the thickness of deposition of inflammatory cells. As can be seen in the figure, in the absence of caspase-1, a central component of the pathway activated by TLR7 and TLR9, the foreign body reaction was significantly reduced.

A 6 mm disc of silicone was implanted subcutaneously in experimental mice (see above), followed by analysis of the foreign body reaction around one month later. The mice were placed on normal drinking water or water with aspirin at a concentration of 60 mg/ml. The experiment resulted in a reduced foreign body reaction in the absence of pathways activated by TLR 7 and 9. FIG. 6 shows that after the implantation of a 6 mm silicone disc the foreign body reaction was quantified by examining the thickness of deposition of inflammatory cells. As can be seen in FIG. 6, in the absence of caspase-1, a central component of the pathway activated by TLR7 and TLR9, the foreign body reaction was substantially reduced.

Figure 7:
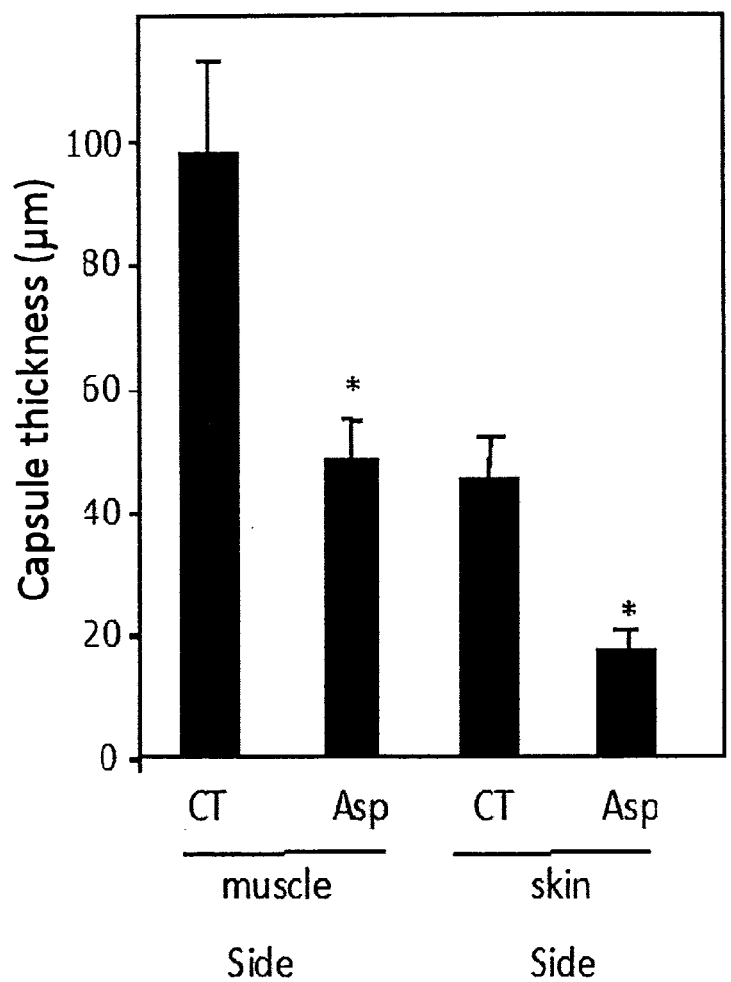
FIG. 7 shows that continuous aspirin in drinking water reduces the thickness of the foreign body reaction in normal mice.

Continuous Aspirin in Drinking Water Reduces the Thickness of the Foreign Body Reaction in Normal Mice Wild-type mice were implanted with a silicone capsule on the side of the muscle and on the side of the skin. The mice were either given regular drinking water or drinking water containing 60 mg/ml aspirin. After one month, the mice were then analyzed to determine if there was an impact on the foreign body reaction which occurred as a consequence of implanting the silicone capsulate. FIG. 7 shows that there is a significant reduction in the thickness of the foreign body reaction capsule on the side of the muscle and on the side of the skin in those wild-type mice who had been receiving aspirin in their drinking water. * indicates $P<0.05$ compared to no ASA.

The experiments presented hereinabove evidence that inhibition of the pathways activated by TLR7 and TLR9 receptors by TLR7, TLR 9 or combined TLR 7/9 antagonists can be used as a favorable therapeutic strategy in a variety of conditions which have in common the presence of sterile inflammation.

Thus, the present invention may be readily used to treat, inhibit or reduce the likelihood of liver injury by drugs, NASH, alcohol and others. The therapeutic aim would be to reduce tissue injury, symptoms and inhibit the progression to fibrosis and cirrhosis. In addition, the present invention may be used in pancreatitis, to reduce pancreatic tissue injury and the severity of pancreatitis. Further, the present invention is useful to treat, inhibit and/or reduce the likelihood of foreign body reaction (inflammation and resulting secondary effects) to biomaterials. The aim of the therapy would be to reduce pain, tenderness, scarring and deformity associated with the implantation of foreign materials and devices. A further aim would be to reduce device failure and extend the residence time and operation of a medical device in a patient, especially including for example, surgical clips and sutures, meshes, and devices such as implantatable insulin pumps, among others.

The invention has been described in detail in order to provide the person of ordinary skill insight and details into the use and application of the present invention. The invention is now further described in the following claims with reference to the above set forth description.

The invention claimed is:

1. A method for reducing, inhibiting or reducing the likelihood of foreign body reaction associated with an implant which produces foreign body reaction in a human patient by increasing proinflammatory cytokines by upregulating a TLR 7/TLR9/NALP3 inflammasome pathway comprising administering to said patient with said implant a pathway inhibiting effective amount of a sustained release composition consisting essentially of a salicylate compound according to the chemical structure:

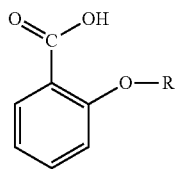

where R is H or a $C_2$-$C_{10}$ acyl group, or a pharmaceutically acceptable salt thereof to said patient, wherein the sustained release administration of said salicylate compound increases the residence time of said implant in said patient by reducing inflammation and scarring associated with said implant and wherein said sustained release composition continuously releases said salicylate in effective amounts.

2. The method according to claim 1 wherein said reduction in the foreign body reaction reduces the likelihood of rejection of said implant by said patient.

3. The method according to claim 1 wherein said administration also reduces one or more of deposition of cells at the site of the implant, pain- and/or swelling at the site of the implant, tenderness at the site of the implant, and infection at the site of the implant in the patient.

4. The method according to claim 1 wherein said administration also reduces deposition of cells at the site of the implant.

5. The method according to claim 4 wherein said cells are neutrophils or macrophages.

6. The method according to claim 1 wherein said administration also reduces pain and/or swelling at the site of the implant.

7. The method according to claim 2 wherein said administration also reduces tenderness at the site of the implant.

8. The method according to claim 2 wherein said administration also reduces infection at the implant.

9. The method according to claim 1 wherein said implant is a pacemaker, a cochlear implant, a subcutaneous drug delivery device, an implantable pill, a drug-eluting stent, a surgical clip, a suture, a surgical mesh, a breast implant, a glucose or insulin sensor, an artificial heart-valve, a bio-implant implanted to replace damaged tissue, a dental implant, an orthopedic implant or a prosthetic device.

10. The method according to claim 1 wherein said implant comprises a biomaterial selected from the group consisting of polymeric materials, metals and ceramics.

11. The method according to claim 9 wherein said implant comprises steel, titanium, silicone, polyester or polypropylene.

12. The method according to claim 1 wherein R is H or a $C_2$ acyl group, or a pharmaceutically acceptable salt thereof.

13. The method according to claim 1 where R is a $C_2$ acyl group or a pharmaceutically acceptable salt thereof.

14. The method according to claim 3 wherein R is H or a $C_2$ acyl group, or a pharmaceutically acceptable salt thereof.

15. The method according to claim 3 where R is a $C_2$ acyl group or a pharmaceutically acceptable salt thereof.

16. The method according to claim 12 wherein said implant is a pacemaker, a cochlear implant, a subcutaneous drug delivery device, an implantable pill, a drug-eluting stent, a surgical clip, a suture, a surgical mesh, a breast implant, a glucose or insulin sensor, an artificial heart-valve, a bio-implant implanted to replace damaged tissue, a dental implant, an orthopedic implant or a prosthetic device.

17. The method according to claim 12 wherein said implant comprises a biomaterial selected from the group consisting of polymeric materials, metals and ceramics.

18. The method according to claim 17 wherein said implant comprises steel, titanium, silicone, polyester or polypropylene.

* * * * *

UNITED STATES PATENT AND TRADEMARK OFFICE
CERTIFICATE OF CORRECTION

PATENT NO. : 9,415,046 B2
APPLICATION NO. : 13/496009
DATED : August 16, 2016
INVENTOR(S) : Wajahat Z. Mehal and Themis Kyriakides Page 1 of 1

It is certified that error appears in the above-identified patent and that said Letters Patent is hereby corrected as shown below:

In the Specification

Column 1, Line 29 Under Related Applications, the second paragraph currently reads:
This invention was made with government support under grant number 1 R01 DK076674-01A2 awarded by the National Institutes of Health. Consequently, the government has certain rights in the invention.

Replace with the following:
This invention was made with government support under DK076674 awarded by National Institutes of Health. The government has certain rights in the invention.

Signed and Sealed this
Seventh Day of July, 2020

Andrei Iancu
*Director of the United States Patent and Trademark Office*

```
                          SEQUENCE LISTING

<160> NUMBER OF SEQ ID NOS: 38

<210> SEQ ID NO 1
<211> LENGTH: 21
<212> TYPE: RNA
<213> ORGANISM: Artificial Sequence
<220> FEATURE:
<223> OTHER INFORMATION: synthetic. phosphorothioate backbone.

<400> SEQUENCE: 1
agaucacccu ccuuaaauau u                                                 21

<210> SEQ ID NO 2
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (4)..(4)
<223> OTHER INFORMATION: um is residue 4, 10, 14, 18.
<220> FEATURE:
<221> NAME/KEY: modified_base
<222> LOCATION: (10)..(10)
<223> OTHER INFORMATION: um is residue 4, 10, 14, 18.
<220> FEATURE:
<221> NAME/KEY: modified_base
<222> LOCATION: (14)..(14)
<223> OTHER INFORMATION: um is residue 4, 10, 14, 18.
<220> FEATURE:
<221> NAME/KEY: modified_base
<222> LOCATION: (18)..(18)
<223> OTHER INFORMATION: um is residue 4, 10, 14, 18.

<400> SEQUENCE: 2
agaucacccu ccuuaaauau u                                                 21

<210> SEQ ID NO 3
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (8)..(8)
<223> OTHER INFORMATION: gm is residue 8. um is residue 17.
<220> FEATURE:
<221> NAME/KEY: modified_base
<222> LOCATION: (17)..(17)
<223> OTHER INFORMATION: gm is residue 8. um is residue 17.

<400> SEQUENCE: 3
uauuuaagga gggugaucuu u                                                 21
```

```
<210> SEQ ID NO 4
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (9)..(9)
<223> OTHER INFORMATION: gm is residue 9, 12, 15.
<220> FEATURE:
<221> NAME/KEY: modified_base
<222> LOCATION: (12)..(12)
<223> OTHER INFORMATION: gm is residue 9, 12, 15.
<220> FEATURE:
<221> NAME/KEY: modified_base
<222> LOCATION: (15)..(15)
<223> OTHER INFORMATION: gm is residue 9, 12, 15.

<400> SEQUENCE: 4
uauuuaagga gggugaucuu u                                             21

<210> SEQ ID NO 5
<211> LENGTH: 10
<212> TYPE: RNA
<213> ORGANISM: Artificial Sequence
<220> FEATURE:
<223> OTHER INFORMATION: synthetic. phosphorothioate backbone. This
      sequence is the 5' oligonucleotide of Seq. Id. 25.
<220> FEATURE:
<221> NAME/KEY: modified_base
<222> LOCATION: (2)..(2)
<223> OTHER INFORMATION: gm is residue 2, 5, 10.
<220> FEATURE:
<221> NAME/KEY: modified_base
<222> LOCATION: (5)..(5)
<223> OTHER INFORMATION: gm is residue 2, 5, 10.
<220> FEATURE:
<221> NAME/KEY: modified_base
<222> LOCATION: (10)..(10)
<223> OTHER INFORMATION: gm is residue 2, 5, 10.

<400> SEQUENCE: 5
ugcuguucug                                                          10

<210> SEQ ID NO 6
<211> LENGTH: 10
<212> TYPE: RNA
<213> ORGANISM: Artificial Sequence
<220> FEATURE:
<223> OTHER INFORMATION: synthetic. phosphorothioate backbone. This
      sequence is the 3' oligonucleotide of Seq. Id. 25.
<220> FEATURE:
<221> NAME/KEY: modified_base
<222> LOCATION: (1)..(1)
<223> OTHER INFORMATION: gm is residue 1, 6, 9.
<220> FEATURE:
<221> NAME/KEY: modified_base
<222> LOCATION: (6)..(6)
<223> OTHER INFORMATION: gm is residue 1, 6, 9.
<220> FEATURE:
<221> NAME/KEY: modified_base
<222> LOCATION: (9)..(9)
<223> OTHER INFORMATION: gm is residue 1, 6, 9.

<400> SEQUENCE: 6
gucuugucgu                                                          10

<210> SEQ ID NO 7
<211> LENGTH: 21
<212> TYPE: RNA
<213> ORGANISM: Artificial Sequence
```

```
<220> FEATURE:
<223> OTHER INFORMATION: synthetic. phosphorothioate backbone.
<220> FEATURE:
<221> NAME/KEY: modified_base
<222> LOCATION: (5)..(5)
<223> OTHER INFORMATION: um is residue 5, 14, 17.
      gm is residue 11.
<220> FEATURE:
<221> NAME/KEY: modified_base
<222> LOCATION: (11)..(11)
<223> OTHER INFORMATION: gm is residue 11.
      um is residue 5, 14, 17.
<220> FEATURE:
<221> NAME/KEY: modified_base
<222> LOCATION: (14)..(14)
<223> OTHER INFORMATION: gm is residue 11.
      um is residue 5, 14, 17.
<220> FEATURE:
<221> NAME/KEY: modified_base
<222> LOCATION: (17)..(17)
<223> OTHER INFORMATION: gm is residue 11.
      um is residue 5, 14, 17.

<400> SEQUENCE: 7
uauuuaagga gggugaucuu u                                              21

<210> SEQ ID NO 8
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (2)..(2)
<223> OTHER INFORMATION: gm is residue 2, 13.
<220> FEATURE:
<221> NAME/KEY: modified_base
<222> LOCATION: (13)..(13)
<223> OTHER INFORMATION: gm is residue 2, 13.

<400> SEQUENCE: 8
agaccuaccu ccggaucaau u                                              21

<210> SEQ ID NO 9
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (6)..(6)
<223> OTHER INFORMATION: um is residue 6, 10, 16.
<220> FEATURE:
<221> NAME/KEY: modified_base
<222> LOCATION: (10)..(10)
<223> OTHER INFORMATION: um is residue 6, 10, 16.
<220> FEATURE:
<221> NAME/KEY: modified_base
<222> LOCATION: (16)..(16)
<223> OTHER INFORMATION: um is residue 6, 10, 16.

<400> SEQUENCE: 9
agaccuaccu ccggaucaau u                                              21

<210> SEQ ID NO 10
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
```

<221> NAME/KEY: modified_base
<222> LOCATION: (5)..(5)
<223> OTHER INFORMATION: um is residue 5, 13, 17.
<220> FEATURE:
<221> NAME/KEY: modified_base
<222> LOCATION: (13)..(13)
<223> OTHER INFORMATION: um is residue 5, 13, 17.
<220> FEATURE:
<221> NAME/KEY: modified_base
<222> LOCATION: (17)..(17)
<223> OTHER INFORMATION: um is residue 5, 13, 17.

<400> SEQUENCE: 10
uugauccgga gguaggucuu u                                              21

<210> SEQ ID NO 11
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (9)..(9)
<223> OTHER INFORMATION: gm is residue 9, 12. um is residue 17.
<220> FEATURE:
<221> NAME/KEY: modified_base
<222> LOCATION: (12)..(12)
<223> OTHER INFORMATION: gm is residue 9, 12. um is residue 17.
<220> FEATURE:
<221> NAME/KEY: modified_base
<222> LOCATION: (17)..(17)
<223> OTHER INFORMATION: gm is residue 9, 12. um is residue 17.

<400> SEQUENCE: 11
uugauccgga gguaggucuu u                                              21

<210> SEQ ID NO 12
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (5)..(5)
<223> OTHER INFORMATION: um is residue 5. gm is residue 8, 11, 16.
<220> FEATURE:
<221> NAME/KEY: modified_base
<222> LOCATION: (8)..(8)
<223> OTHER INFORMATION: um is residue 5. gm is residue 8, 11, 16.
<220> FEATURE:
<221> NAME/KEY: modified_base
<222> LOCATION: (11)..(11)
<223> OTHER INFORMATION: um is residue 5. gm is residue 8, 11, 16.
<220> FEATURE:
<221> NAME/KEY: modified_base
<222> LOCATION: (16)..(16)
<223> OTHER INFORMATION: um is residue 5. gm is residue 8, 11, 16.

<400> SEQUENCE: 12
uugauccgga gguaggucuu u                                              21

<210> SEQ ID NO 13
<211> LENGTH: 21
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: misc_feature
<222> LOCATION: (1)..(19)
<223> OTHER INFORMATION: RNA segment

```
<220> FEATURE:
<221> NAME/KEY: modified_base
<222> LOCATION: (2)..(2)
<223> OTHER INFORMATION: um is residue 2, 10, 19.
<220> FEATURE:
<221> NAME/KEY: modified_base
<222> LOCATION: (10)..(10)
<223> OTHER INFORMATION: um is residue 2, 10, 19.
<220> FEATURE:
<221> NAME/KEY: modified_base
<222> LOCATION: (19)..(19)
<223> OTHER INFORMATION: um is residue 2, 10, 19.
<220> FEATURE:
<221> NAME/KEY: misc_feature
<222> LOCATION: (20)..(21)
<223> OTHER INFORMATION: DNA segment

<400> SEQUENCE: 13
cugaagaccu gaagacaaut t                                              21

<210> SEQ ID NO 14
<211> LENGTH: 21
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: misc_feature
<222> LOCATION: (1)..(19)
<223> OTHER INFORMATION: RNA segment
<220> FEATURE:
<221> NAME/KEY: modified_base
<222> LOCATION: (3)..(3)
<223> OTHER INFORMATION: gm is rresidue 3, 6, 11, 14.
<220> FEATURE:
<221> NAME/KEY: modified_base
<222> LOCATION: (6)..(6)
<223> OTHER INFORMATION: gm is rresidue 3, 6, 11, 14.
<220> FEATURE:
<221> NAME/KEY: modified_base
<222> LOCATION: (11)..(11)
<223> OTHER INFORMATION: gm is rresidue 3, 6, 11, 14.
<220> FEATURE:
<221> NAME/KEY: modified_base
<222> LOCATION: (14)..(14)
<223> OTHER INFORMATION: gm is rresidue 3, 6, 11, 14.
<220> FEATURE:
<221> NAME/KEY: misc_feature
<222> LOCATION: (20)..(21)
<223> OTHER INFORMATION: DNA segment

<400> SEQUENCE: 14
cugaagaccu gaagacaaut t                                              21

<210> SEQ ID NO 15
<211> LENGTH: 21
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: misc_feature
<222> LOCATION: (1)..(19)
<223> OTHER INFORMATION: RNA segment.
<220> FEATURE:
<221> NAME/KEY: modified_base
<222> LOCATION: (8)..(8)
<223> OTHER INFORMATION: um is residue 8, 13, 16.
<220> FEATURE:
<221> NAME/KEY: modified_base
<222> LOCATION: (13)..(13)
<223> OTHER INFORMATION: um is residue 8, 13, 16.
<220> FEATURE:
<221> NAME/KEY: modified_base
<222> LOCATION: (16)..(16)
```

```
<223> OTHER INFORMATION: um is residue 8, 13, 16.
<220> FEATURE:
<221> NAME/KEY: misc_feature
<222> LOCATION: (20)..(21)
<223> OTHER INFORMATION: DNA segment.

<400> SEQUENCE: 15
auugucuuca ggucuucagt t                                              21

<210> SEQ ID NO 16
<211> LENGTH: 21
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: misc_feature
<222> LOCATION: (1)..(19)
<223> OTHER INFORMATION: RNA segment.
<220> FEATURE:
<221> NAME/KEY: modified_base
<222> LOCATION: (4)..(4)
<223> OTHER INFORMATION: gm is residue 4, 12, 19.
<220> FEATURE:
<221> NAME/KEY: modified_base
<222> LOCATION: (12)..(12)
<223> OTHER INFORMATION: gm is residue 4, 12, 19.
<220> FEATURE:
<221> NAME/KEY: modified_base
<222> LOCATION: (19)..(19)
<223> OTHER INFORMATION: gm is residue 4, 12, 19.
<220> FEATURE:
<221> NAME/KEY: misc_feature
<222> LOCATION: (20)..(21)
<223> OTHER INFORMATION: DNA segment.

<400> SEQUENCE: 16
auugucuuca ggucuucagt t                                              21

<210> SEQ ID NO 17
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (3)..(3)
<223> OTHER INFORMATION: um is residue 3, 6, 8, 13, 14, 16, 18.
<220> FEATURE:
<221> NAME/KEY: modified_base
<222> LOCATION: (6)..(6)
<223> OTHER INFORMATION: um is residue 3, 6, 8, 13, 14, 16, 18.
<220> FEATURE:
<221> NAME/KEY: modified_base
<222> LOCATION: (8)..(8)
<223> OTHER INFORMATION: um is residue 3, 6, 8, 13, 14, 16, 18.
<220> FEATURE:
<221> NAME/KEY: modified_base
<222> LOCATION: (13)..(14)
<223> OTHER INFORMATION: um is residue 3, 6, 8, 13, 14, 16, 18.
<220> FEATURE:
<221> NAME/KEY: modified_base
<222> LOCATION: (16)..(16)
<223> OTHER INFORMATION: um is residue 3, 6, 8, 13, 14, 16, 18.
<220> FEATURE:
<221> NAME/KEY: modified_base
<222> LOCATION: (18)..(18)
<223> OTHER INFORMATION: um is residue 3, 6, 8, 13, 14, 16, 18.

<400> SEQUENCE: 17
gauuaugucc gguuauguau u                                              21
```

```
<210> SEQ ID NO 18
<211> LENGTH: 21
<212> TYPE: RNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (5)..(5)
<223> OTHER INFORMATION: um is residue 5, 15, 18.
<220> FEATURE:
<221> NAME/KEY: modified_base
<222> LOCATION: (15)..(15)
<223> OTHER INFORMATION: um is residue 5, 15, 18.
<220> FEATURE:
<221> NAME/KEY: modified_base
<222> LOCATION: (18)..(18)
<223> OTHER INFORMATION: um is residue 5, 15, 18.

<400> SEQUENCE: 18
uacauaaccg gacauaaucu u                                              21

<210> SEQ ID NO 19
<211> LENGTH: 18
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (7)..(7)
<223> OTHER INFORMATION: gm is residue 7. 2'-O-methyladenosine is
      residue 8.
<220> FEATURE:
<221> NAME/KEY: modified_base
<222> LOCATION: (8)..(8)
<223> OTHER INFORMATION: gm is residue 7. 2'-O-methyladenosine is
      residue 8.

<400> SEQUENCE: 19
ctatctgacg ttctctgt                                                  18

<210> SEQ ID NO 20
<211> LENGTH: 18
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (7)..(7)
<223> OTHER INFORMATION: gm is residue 7. uracil is residue 8.
<220> FEATURE:
<221> NAME/KEY: modified_base
<222> LOCATION: (8)..(8)
<223> OTHER INFORMATION: gm is residue 7. uracil is residue 8.
<220> FEATURE:
<221> NAME/KEY: misc_feature
<222> LOCATION: (8)..(8)
<223> OTHER INFORMATION: uracil is a modified base for a DNA sequence.

<400> SEQUENCE: 20
ctatctgncg ttctctgt                                                  18

<210> SEQ ID NO 21
<211> LENGTH: 18
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (7)..(7)
```

```
<223> OTHER INFORMATION: gm is residue 7. 2'-O-methyladenosine is
      residue 8.
<220> FEATURE:
<221> NAME/KEY: modified_base
<222> LOCATION: (8)..(8)
<223> OTHER INFORMATION: gm is residue 7. 2'-O-methyladenosine is
      residue 8.
<220> FEATURE:
<221> NAME/KEY: modified_base
<222> LOCATION: (10)..(10)
<223> OTHER INFORMATION: gm is residue 7. 2'-O-methyladenosine is
      residue 8. 2'-deoxy-7-deazaguanosine is residue 10.

<400> SEQUENCE: 21
ctatctgacg ttctctgt                                                  18

<210> SEQ ID NO 22
<211> LENGTH: 18
<212> TYPE: DNA
<213> ORGANISM: Artificial Sequence
<220> FEATURE:
<223> OTHER INFORMATION: synthetic. phosphorothioate backbone.
<220> FEATURE:
<221> NAME/KEY: modified_base
<222> LOCATION: (7)..(7)
<223> OTHER INFORMATION: gm is residue 7. uracil is residue 8.
      2'-deoxy-7-deazaguanosine is residue 10.
<220> FEATURE:
<221> NAME/KEY: modified_base
<222> LOCATION: (8)..(8)
<223> OTHER INFORMATION: gm is residue 7. uracil is residue 8.
      2'-deoxy-7-deazaguanosine is residue 10.
<220> FEATURE:
<221> NAME/KEY: misc_feature
<222> LOCATION: (8)..(8)
<223> OTHER INFORMATION: uracil is a modified base for a DNA sequence.
<220> FEATURE:
<221> NAME/KEY: modified_base
<222> LOCATION: (10)..(10)
<223> OTHER INFORMATION: gm is residue 7. uracil is residue 8.
      2'-deoxy-7-deazaguanosine is residue 10.

<400> SEQUENCE: 22
ctatctgncg ttctctgt                                                  18

<210> SEQ ID NO 23
<211> LENGTH: 15
<212> TYPE: DNA
<213> ORGANISM: Artificial Sequence
<220> FEATURE:
<223> OTHER INFORMATION: synthetic. phosphorothioate backbone.

<400> SEQUENCE: 23
tcctggaggg gaagt                                                     15

<210> SEQ ID NO 24
<211> LENGTH: 15
<212> TYPE: DNA
<213> ORGANISM: Artificial Sequence
<220> FEATURE:
<223> OTHER INFORMATION: synthetic. phosphorothioate backbone.

<400> SEQUENCE: 24
tcctggcggg gaagt                                                     15

<210> SEQ ID NO 25
<211> LENGTH: 21
<212> TYPE: RNA
<213> ORGANISM: Artificial Sequence
<220> FEATURE:
<223> OTHER INFORMATION: synthetic. phosphorothioate backbone.
```

```
<220> FEATURE:
<221> NAME/KEY: modified_base
<222> LOCATION: (11)..(11)
<223> OTHER INFORMATION: a glycerol linker is residue 11. The component
      5' oligonucleotide is also presented in Seq. Id. 5. The component
      3' oligonucleotide is also presented in Seq. Id. 6.
<220> FEATURE:
<221> NAME/KEY: misc_feature
<222> LOCATION: (11)..(11)
<223> OTHER INFORMATION: glycerol linker: see: J. Med. Chem., 2009, 5,
      551-558 and J. Med. Chem., 2009, 52, 5108-5114.

<400> SEQUENCE: 25
ugcuguucug ngucuugucg u                                              21

<210> SEQ ID NO 26
<211> LENGTH: 15
<212> TYPE: DNA
<213> ORGANISM: Artificial Sequence
<220> FEATURE:
<223> OTHER INFORMATION: synthetic

<400> SEQUENCE: 26
tcctggcggg gaagt                                                     15

<210> SEQ ID NO 27
<211> LENGTH: 15
<212> TYPE: DNA
<213> ORGANISM: Artificial Sequence
<220> FEATURE:
<223> OTHER INFORMATION: synthetic

<400> SEQUENCE: 27
tcctggaggg gaagt                                                     15

<210> SEQ ID NO 28
<211> LENGTH: 15
<212> TYPE: DNA
<213> ORGANISM: Artificial Sequence
<220> FEATURE:
<223> OTHER INFORMATION: synthetic

<400> SEQUENCE: 28
tcctggatgg gaagt                                                     15

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
cctggatggg aattcccatc cagg                                           24

<210> SEQ ID NO 30
<211> LENGTH: 24
<212> TYPE: DNA
<213> ORGANISM: Artificial Sequence
<220> FEATURE:
<223> OTHER INFORMATION: synthetic

<400> SEQUENCE: 30
ttcccatcca ggcctggatg ggaa                                           24

<210> SEQ ID NO 31
<211> LENGTH: 24
```

```
<212> TYPE: DNA
<213> ORGANISM: Artificial Sequence
<220> FEATURE:
<223> OTHER INFORMATION: synthetic

<400> SEQUENCE: 31
cctggatggg aacttaccgc tgca                                          24

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
gggggggggg gggggggggg                                               20

<210> SEQ ID NO 33
<211> LENGTH: 24
<212> TYPE: DNA
<213> ORGANISM: Artificial Sequence
<220> FEATURE:
<223> OTHER INFORMATION: synthetic

<400> SEQUENCE: 33
ttagggttag ggttagggtt aggg                                          24

<210> SEQ ID NO 34
<211> LENGTH: 22
<212> TYPE: DNA
<213> ORGANISM: Artificial Sequence
<220> FEATURE:
<223> OTHER INFORMATION: synthetic

<400> SEQUENCE: 34
tgactgtgaa ggttagagat ga                                            22

<210> SEQ ID NO 35
<211> LENGTH: 21
<212> TYPE: DNA
<213> ORGANISM: Artificial Sequence
<220> FEATURE:
<223> OTHER INFORMATION: synthetic

<400> SEQUENCE: 35
ctcctattgg gggtttccta t                                             21

<210> SEQ ID NO 36
<211> LENGTH: 15
<212> TYPE: DNA
<213> ORGANISM: Artificial Sequence
<220> FEATURE:
<223> OTHER INFORMATION: synthetic

<400> SEQUENCE: 36
tcctggaggg gttgt                                                    15

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
```

```
tgcttgcaag cttgcaagca                                              20

<210> SEQ ID NO 38
<211> LENGTH: 18
<212> TYPE: DNA
<213> ORGANISM: Artificial Sequence
<220> FEATURE:
<223> OTHER INFORMATION: synthetic

<400> SEQUENCE: 38
tgctcctgga ggggttgt                                                18
```